US008101823B2

(12) United States Patent
Werner et al.

(10) Patent No.: US 8,101,823 B2
(45) Date of Patent: Jan. 24, 2012

(54) METHOD OF CONTROLLING A CELLULAR PROCESS IN A MULTI-CELLULAR ORGANISM

(75) Inventors: Stefan Werner, Halle/Saale (DE); Sylvestre Marillonnet, Halle/Saale (DE); Yurii Dorokhov, Moscow (RU); Victor Klimyuk, Halle/Saale (DE); Yuri Gleba, Halle/Saale (DE)

(73) Assignee: Icon Genetics GmbH, München (DE)

( * ) Notice: Subject to any disclaimer, the term of this patent is extended or adjusted under 35 U.S.C. 154(b) by 324 days.

(21) Appl. No.: 10/535,763

(22) PCT Filed: Nov. 20, 2003

(86) PCT No.: PCT/EP03/13021
§ 371 (c)(1),
(2), (4) Date: May 20, 2005

(87) PCT Pub. No.: WO2004/046361
PCT Pub. Date: Jun. 3, 2004

(65) Prior Publication Data
US 2006/0075524 A1    Apr. 6, 2006

(30) Foreign Application Priority Data
Nov. 20, 2002    (EP) ..................... 10254165

(51) Int. Cl.
*C12N 15/82*    (2006.01)
*C12N 15/29*    (2006.01)
*C12N 15/00*    (2006.01)
*A01H 5/00*    (2006.01)

(52) U.S. Cl. ........ 800/294; 800/278; 800/288; 800/295; 435/320.1; 435/468; 536/23.1; 536/23.2; 536/24.1

(58) Field of Classification Search ........................ None
See application file for complete search history.

(56) References Cited

U.S. PATENT DOCUMENTS
2002/0046419 A1    4/2002    Choo et al.
2002/0143142 A1    10/2002    Lin et al.

FOREIGN PATENT DOCUMENTS
JP    2000-500323    1/2000
WO    WO 95/21248 A1    8/1995
WO    WO9521248    *    8/1995
WO    WO 98/37211    8/1998
WO    WO 99/52563 A1    10/1999
WO    WO0071701    *    5/2000
WO    WO 00/52146 A2    9/2000
WO    WO 00/52146 A3    9/2000
WO    WO 00/71701 A1    11/2000
WO    WO 01/38488 A2    5/2001
WO    WO0189283    *    5/2001
WO    WO0189283    *    11/2001

OTHER PUBLICATIONS

Mackenzie 2005 Trends in Cell Biology 15:548-554.*
Jo, E., et al., "Epigenetic Regulation of Gene Structure and Function with a Cell-Permeable Cre Recombinase," *Nature Biotechnology*, 2001, pp. 929-933, vol. 19, Nature Publishing Group.
Will, E., et al., "Unmodified Cre Recombinase Crosses the Membrane," *Nucleic Acids Research*, 2002, pp. 1-6, vol. 30(12)e59, Oxford University Press.
Zhang, Y., et al., "Efficient and Inducible Production of Human Interleukin 6 in Chinese Hamster Ovary Cells Using a Novel Expression System," *Cytotechnology*, 1997, pp. 53-60, vol. 25, Kluwer Academic Publishers, Netherlands.
O'Donnell, P., et al., "A Novel Tomato Gene that Rapidly Responds to Wound- and Pathogen-Related Signals," *The Plant Journal*, 1998, pp. 137-142, vol. 14(1), Blackwell Science Ltd.
Pearce, G., et al., "A Polypeptide from Tomato Leaves Induces Wound-Inducible Proteinase Inhibitor Proteins," *Science Reports*, 1991, pp. 895-898, vol. 23.
Thyagarajan, B., et al., "Mammalian genomes contain active recombinase sites," *Gene*, 2000, vol. 244, pp. 47-54.
Schmidt, E., et al., "Illegitimate Cre-dependent chromosome rearrangements in transgenic mouse spermatids," *PNAS*, 2000, vol. 97(25), pp. 13702-13707.
"Chemistry of Organisms—Chemistry in Treating Diseases from Gene Therapy to Protein Therapy," *Chemistry*, 2002, vol. 57(9), pp. 50-55.
Gelvin, Stanton B., *Agrobaterium*-Mediated Plant Transformation: the Biology behind the "Gene-Jockeying" Tool, Microbiology and Molecular Biology Reviews, Mar. 2003, vol. 67, No. 1, p. 16-37.

* cited by examiner

*Primary Examiner* — Brent T Page
(74) *Attorney, Agent, or Firm* — Alston & Bird LLP

(57) ABSTRACT

A method of controlling a genetically-modified multi-cellular organism or a part thereof, comprising the following steps: (a) providing a multi-cellular organism or a part thereof, whereby cells of said multi-cellular organism or said part contain a heterologous nucleic acid, (b) causing expression of a I protein from said heterologous nucleic acid in at least some of said cells, wherein said protein is capable of (i) leaving a cell and entering other cells of said multi-cellular organism or a part thereof, (ii) causing expression of said protein in cells containing said heterologous nucleic acid, and optionally (iii) controlling a cellular process of interest.

11 Claims, 8 Drawing Sheets

SEQUENCE LISTING

<160> NUMBER OF SEQ ID NOS: 7

<210> SEQ ID NO 1
<211> LENGTH: 5
<212> TYPE: PRT
<213> ORGANISM: Artificial Sequence
<220> FEATURE:
<223> OTHER INFORMATION: enterokinase cleavage site

<400> SEQUENCE: 1

Asp Asp Asp Lys Ile
1               5

<210> SEQ ID NO 2
<211> LENGTH: 11
<212> TYPE: PRT
<213> ORGANISM: Artificial Sequence

```
<220> FEATURE:
<223> OTHER INFORMATION: Membrane Transloacation Signal

<400> SEQUENCE: 2

Arg Arg Arg Arg Arg Arg Arg Arg Arg Arg
1               5                   10

<210> SEQ ID NO 3
<211> LENGTH: 27
<212> TYPE: PRT
<213> ORGANISM: Artificial Sequence
<220> FEATURE:
<223> OTHER INFORMATION: Membrane Transloacation Signal

<400> SEQUENCE: 3

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 4
<211> LENGTH: 9
<212> TYPE: PRT
<213> ORGANISM: Human immunodeficiency virus

<400> SEQUENCE: 4

Arg Lys Lys Arg Arg Gln Arg Arg Arg
1               5

<210> SEQ ID NO 5
<211> LENGTH: 16
<212> TYPE: PRT
<213> ORGANISM: Artificial Sequence
<220> FEATURE:
<223> OTHER INFORMATION: Membrane Transloacation Signal

<400> SEQUENCE: 5

Arg Gln Ile Lys Ile Trp Phe Gln Asn Arg Arg Met Lys Trp Lys Lys
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Membrane Transloacation Signal

<400> SEQUENCE: 6

Ala Ala Val Ala Leu Leu Pro Ala Val Leu Leu Ala Leu Leu Ala Pro
1               5                   10                  15

<210> SEQ ID NO 7
<211> LENGTH: 21
<212> TYPE: PRT
<213> ORGANISM: Artificial Sequence
<220> FEATURE:
<223> OTHER INFORMATION: Membrane Transloacation Signal

<400> SEQUENCE: 7

Lys Glu Thr Trp Trp Glu Thr Trp Trp Thr Glu Trp Ser Gln Pro Lys
1               5                   10                  15

Lys Lys Arg Lys Val
            20
```

METHOD OF CONTROLLING A CELLULAR PROCESS IN A MULTI-CELLULAR ORGANISM

FIELD OF THE INVENTION

The present invention relates to a method of controlling a cellular process of interest in a multi-cellular organism, notably in plants. Further, the present invention relates to a genetically-modified multi-cellular organism and to a system for performing the method of the invention. The process of the invention allows e.g. for the selective control over transgene expression in a transiently or stably genetically-modified multicellular organism, whereby a biochemical process or biochemical cascade of interest previously non-operable in the multicellular organism may be selectively switched on at a predetermined time.

BACKGROUND OF THE INVENTION

Controllable Transgene Expression Systems in Plants

One of the major problems in plant biotechnology is the achievement of a reliable control over transgene expression. Tight control over gene expression in plants is essential if a downstream product of transgene expression is growth inhibitory or toxic, like for example, biodegradable plastics (Nawrath, Poirier & Somerville, 1994, *Proc. Natl. Acad. Sci.*, 91, 12760-12764; John & Keller, 1996, *Proc. Natl. Acad. Sci.*, 93, 12768-12773; U.S. Pat. No. 6,103,956; U.S. Pat. No. 5,650,555) or protein toxins (U.S. Pat. No. 6,140,075).

Existing technologies for controlling gene expression in multicellular organisms, especially in plants, are usually based on tissue-specific or inducible promoters and practically all of them suffer from a basal expression activity even when uninduced, i.e. they are "leaky". Tissue-specific promoters (U.S. Pat. No. 0,595,5361; WO09828431) represent a powerful tool but their use is restricted to very specific areas of applications, e.g. for producing sterile plants (WO9839462) or expressing genes of interest in seeds (WO00068388; U.S. Pat. No. 0,560,8152). Inducible promoters can be divided into two categories according to their induction conditions: those induced by abiotic factors (temperature, light, chemical substances) and those that can be induced by biotic factors, for example, pathogen or pest attack. Examples of the first category are heat-inducible (U.S. Pat. No. 0,518,7287) and cold-inducible (U.S. Pat. No. 0,584,7102) promoters, a copper-inducible system (Mett et al., 1993, *Proc. Natl. Acad. Sci.*, 90, 4567-4571), steroid-inducible systems (Aoyama & Chua, 1997, *Plant J.*, 11, 605-612; McNellis et al., 1998, *Plant J.*, 14, 247-257; U.S. Pat. No. 0,606,3985), an ethanol-inducible system (Caddick et al., 1997, *Nature Biotech.*, 16, 177-180; WO09321334), and a tetracycline-inducible system (Weinmann et al., 1994, *Plant J.*, 5, 559-569). One of the latest developments in the area of chemically inducible systems for plants is a chimaeric promoter that can be switched on by the glucocorticoid dexamethasone and switched off by tetracycline (Bohner et al., 1999, *Plant J.*, 19, 87-95). For a review on chemically inducible systems see: Zuo & Chua, (2000, *Current Opin. Biotechnol.*, 11, 146-151). Other examples of inducible promoters are promoters which control the expression of pathogenesis-related (PR) genes in plants. These promoters can be induced by treatment of a plant with salicylic acid, an important component of plant signaling pathways in response to pathogen attack, or other chemical compounds (benzo-1,2,3-thiadiazole or isonicotinic acid) which are capable of triggering PR gene expression (U.S. Pat. No. 5,942,662).

There are reports of controllable transgene expression systems using viral RNA/RNA polymerase provided by viral infection (for example, see U.S. Pat. No. 6,093,554; U.S. Pat. No. 5,919,705). In these systems, a recombinant plant DNA sequence includes the nucleotide sequences from the viral genome recognized by viral RNA/RNA polymerase. The effectiveness of these systems is limited because of the low ability of viral polymerases to provide functions in trans, and their inability to control processes other than RNA amplification.

Another way is to trigger a process of interest in a transgenic plant is by using a genetically-modified virus which provides a heterologous nucleic acid encoding a switch for a biochemical process in a genetically-modified plant (WO02068664).

The systems described above are of significant interest as opportunities of obtaining desired patterns of transgene expression, but they do not allow tight control over the expression patterns, as the inducing agents (copper) or their analogs (brassinosteroids in case of steroid-controllable system) can be present in plant tissues at levels sufficient to cause residual expression. Additionally, the use of antibiotics and steroids as chemical inducers is not desirable or economically unfeasible for large-scale applications. When using promoters of PR genes or viral RNA/RNA polymerases as control means for transgenes, the requirements of tight control over transgene expression are also not fulfilled, as casual pathogen infection or stress can cause expression. Tissue- or organ-specific promoters are restricted to very narrow areas of application, since they confine expression to a specific organ or stage of plant development, but do not allow the transgene to be switched on at will. Recombinant viral switches as described in WO02068664 address all these problems, but do not guarantee tight environmental safety requirements, as the heterologous nucleic acid in the viral vector can recombine.

There is an abundant literature including patent applications which describe the design of virus resistant plants by the expression of viral genes or mutated forms of viral RNA (e.g. U.S. Pat. No. 5,792,926; U.S. Pat. No. 6,040,496). It is also worth mentioning that an environmental risk is associated with the use of such plants due to the possibility of forming novel viruses by recombination between the challenging virus and transgenic viral RNA or DNA (Adair & Kearney, 2000, *Arch. Virol*, 145, 1867-1883).

Protein-protein interactions as switch of gene expression represent an interesting choice due to several advantages over the existing controllable systems. The system built on protein-protein interactions may be rendered highly specific, as the function of interest is a result of a highly specific protein-protein or protein-nucleic acid interaction, which is characterized by near zero-level expression in the uninduced state and absence of non-specific leakiness in cases when the activation of gene of interest is dependent on nucleic acid (DNA or RNA) rearrangement, said nucleic acid is encoding and/or controlling said gene. This is in contrast to existing systems such as switches based on small molecules that are inherently less specific and invariably show a certain degree of leakiness.

However, all systems described above suffer from at least one of the following two severe problems: (i) the lack of tightly controlled regulation, e.g. "leakiness" of the system; (ii) the induction of a cellular process is usually restricted to a limited number of cells within a multicellular organism, especially in the case of a tightly regulated and highly specific regulatory system built on e.g. protein-protein or protein-nucleic acid interactions. Usually the tighter the regulation, the smaller is the number of cells in a multi-cellular organism that can be affected by an externally applied signal for inducing the cellular process of interest. An example of this problem are the publications of Hooykaas and colleagues (2000, *Science,* 290, 979-982; WO0189283) describing a specifically triggered process of expressing a gene of interest conferring antibiotic resistance to plant cells. This process is specifically triggered by the externally delivered enzyme Cre recombinase. However, the efficiency of applying the external trigger is low, as Cre recombinase can be delivered only to a small fraction of the target cells. As a result, cells expressing the resistance gene can be detected in tissue culture due to their selectable phenotype caused by antibiotic resistance. However, this method is limited to issue culture and cannot be applied to whole multi-cellular organisms like higher plants.

Therefore, it is an object of the present invention to provide an environmentally safe method of controlling a cellular process of interest in a multi-cellular organism, notably a higher plant, whereby the cellular process can be efficiently and selectively activated in said multi-cellular organism or a part thereof. It is another object of the invention to provide a method for producing a product in a genetically-modified multi-cellular organism, notably a higher plant, wherein the production of the product may be selectively switched on after the multi-cellular organism has grown to a desired stage.

GENERAL DESCRIPTION OF THE INVENTION

The above objects are achieved by a method of controlling a genetically-modified multi-cellular organism or a part thereof, comprising the following steps:
(a) providing a multi-cellular organism or a part thereof, whereby cells of said multi-cellular organism or said part contain a heterologous nucleic acid,
(b) causing expression of a protein from said heterologous nucleic acid in at least some of said cells,
wherein said protein is capable of
(i) leaving a cell and entering other cells of said multi-cellular organism or a part thereof,
(ii) causing expression of said protein in cells containing said heterologous nucleic acid, and optionally
(iii) controlling a cellular process of interest.

The invention also provides genetically-modified multi-cellular organisms or parts thereof obtained or obtainable by the method of the invention. Preferably, the invention provides genetically-modified multi-cellular plants or parts thereof obtained by said method. Preferred parts of a plant obtained or obtainable by said method are leaves and seeds. Seeds are most preferred examples for parts of a plant.

The invention further provides a genetically-modified multi-cellular organism or a part thereof containing a heterologous nucleic acid in cells thereof, whereby said heterologous nucleic acid is adapted such that
(a) expression of a protein from said heterologous nucleic acid can be caused in cells containing said heterologous nucleic and
(b) said protein is capable of leaving a cell and entering other cells of said multi-cellular organism or a part thereof, and
(c) said control protein is capable of controlling an expression of said protein in cells containing said heterologous nucleic acid and
(d) optionally, controlling a cellular process of interest.

The invention further provides a system for controlling expression of protein, comprising a genetically-modified multi-cellular organism as defined herein and a signal for causing expression of said protein, whereby said multi-cellular organism and said signal are designed such that expression of said protein can be initiated by externally applying said signal to said multi-cellular organism or a part thereof.

The invention also provides a composition for external application to a multi-cellular organism as defined above, whereby said composition contains a polypeptide or protein as defined herein, said polypeptide or protein being a signal for causing expression of a protein in a genetically-modified multi-cellular organism as defined above.

Further embodiments are defined in the claims and subclaims.

The present invention allows to control a multi-cellular organism or a part thereof by causing (inducing) expression of said protein (also referred to herein as "control protein" or as "protein switch") in some of the cells of said multi-cellular organism. Preferably, controlling said multi-cellular organism or a part thereof includes controlling a cellular process of interest. Expression of said control protein is preferably caused by an externally applied signal. Said control protein is capable of controlling said cellular process of interest in cells in which said control protein is expressed. Further, said control protein is capable of spreading to other cells of said multi-cellular organism. In other cells of said multi-cellular organism, said control protein is capable of controlling said cellular process of interest and of causing expression of more copies of said control protein. Thus, said control protein is capable of causing its own expression, notably in cells of said multi-cellular organism in which expression of said control protein was not caused by said externally applied signal. As a result, once expression of said control protein was induced in some cells of said multi-cellular organism, said control protein can carry said externally applied signal in an avalanche-like way to other cells and other parts of said multi-cellular organism that were not reached by said externally applied signal. Due to the capability of said control protein of the invention to control a cellular process of interest in a multi-cellular organism, it is also referred to herein as "protein switch".

In the method of the invention, a cellular process of interest is controlled in a genetically-modified multi-cellular organism or a part thereof. Said genetically-modified multi-cellular organism may be an animal, a fungus, or a plant. Plants are preferred. Among animals, vertebrates are preferred and mammals are most preferred, but humans are excluded. Among plants, higher plants, notably higher crop plants, are preferred. A part of a multi-cellular organism according to the invention may be a certain tissue or organ. The method of the invention may be carried out on isolated (separated from the multi-cellular organism) tissues or organs as far as methods of maintaining such tissues (e.g. tissue culture) or organs separated from their organisms of origin are available. Important parts of a genetically-modified multi-cellular plant are seeds of said plant.

In order to make full use of the potential of the present invention, the method of the invention is applied to entire multi-cellular organisms, notably entire plants. If one works with entire multi-cellular organism, the control over said cellular process of interest does not have to affect the entire multi-cellular organism. Instead, the control over said cellular process of interest may be limited to a part of said multi-cellular organism. Preferably, however, said controlling affects substantial parts of said multi-cellular organism. The part of a multi-cellular organism where said cellular process is controlled depends inter alia on the type and especially on the place(s) of application of said externally applied signal that causes expression of said control protein. Generally, control may be strongest in the vicinity of the place of application of the external signal and may decrease with increasing distance from said place. Said decrease of said control may in general be anisotropic and depend on the structure of the tissue of said multi-cellular organism where the external signal was applied. If, for example, a cellular process of interest is to be switched on in a plant (e.g. expression of a gene of interest is to be switched on) and said external signal is applied to a fraction of a leaf of the plant, said cellular process of interest typically occurs within said fraction of said leaf and in the vicinity of said fraction of said leaf. Preferably, said cellular process of interest occurs in the major part of said leaf. More preferably, said cellular process of interest occurs also in the shoot and in other leaves. Most preferably, said cellular process of interest occurs in the major part of said plant. The extent of said cellular process of interest (e.g. expression of a gene of interest) may vary within said plant e.g. with the cell type or tissue type. Obviously, application of said external signal is normally not limited to a single point on the surface of a multi-cellular organism. Preferably, said external signal is applied to several parts of said multi-cellular organism (see further below).

In step (a) of the method of the invention, a genetically-modified multi-cellular organism or a part thereof is provided. Said multi-cellular organism or said part is genetically-modified in that cells of the organism contain a heterologous nucleic acid from which said control protein can be expressed. Said heterologous nucleic acid preferably encodes said control protein. Alternatively, said heterologous nucleic acid may encode said control protein after a reorganization caused by said external signal or said control protein. As an example of this alternative, the heterologous nucleic acid may encode said control protein after a recombination caused e.g. by a recombinase activity of said external signal.

Said multi-cellular organism provided in step (a) may be a transgenic multi-cellular organism, whereby most or all of the cells of said organism contain said heterologous nucleic acid stably integrated in the genome of said cells. Said heterologous nucleic acid may be stably integrated into the nuclear genome or in the genome of organelles like mitochondria or, in the case of plants, plastids. In the case of plants, integration of said heterologous nucleic acid in the plastid genome is advantageous in terms of biological safety. The method of the invention is preferably carried out with transgenic multi-cellular organisms. Alternatively, however, said organism may be transiently modified and/or said heterologous nucleic acid may be present in a fraction of cells of said organism but not in other cells. A heterologous nucleic acid in a transiently modified multi-cellular organism may be stably integrated in the genome of said fraction of cells or it may be present episomally. Incorporation of said heterologous nucleic acid in a fraction of cells of said organism may be achieved by transiently transfecting said organism e.g. using viral transfection or *Agrobacterium*-mediated transformation.

In step (b) of the method of the invention, expression of said control protein from said heterologous nucleic acid is induced in at least some of said cells containing said heterologous nucleic acid. Said expression is typically caused by applying an external signal to cells of said multi-cellular organism that contain said heterologous nucleic acid. If said organism is transgenic, said signal may in principal be applied to any part or to any cells of the organism. If only a fraction of the cells of said organism contains said heterologous nucleic acid, said signal is applied to the organism such that said external signal can reach one or more cells containing said heterologous nucleic acid for causing expression of said control protein (protein switch). Examples of such external signals are the following: small molecular organic compound, metal ions, polypeptides, nucleic acids, pathogens, viruses, bacteria, fungi, light, temperature change, or other biotic or abiotic factors. Among these external signals, a polypeptide, a nucleic acid, a pathogen, a virus and a bacterium are preferred. A polypeptide is most preferred. Naturally, the application methods of these signals should be adjusted to the type of signal used. In the case of small molecular organic compound, metal ions, polypeptides, nucleic acids, pathogens, viruses, bacteria, and fungi, said signals may be applied e.g. by spraying said organism, notably a plant, with a solution or a suspension containing the respective signal. Further application methods are described below. Many others are generally known in the art.

In the preferred case of a polypeptide as said external signal, said polypeptide preferably comprises a membrane translocation sequence that enables entering of said polypeptide into cells of said multicellular organism. Said membrane translocation sequence may be covalently or non-covalently bound to said polypeptide. Preferably, it is covalently bound to said polypeptide. Said membrane translocation sequence may be a peptide that endows said polypeptide with the capability of crossing the plasma membrane of cells of said organism. Many such membrane translocation sequences are known in the art. Frequently, they comprise several basic amino acids, notably arginines. The size of membrane translocation sequences may vary largely, however, they may typically have 3 to 100 amino acids, preferably 5 to 60 amino acids. Said polypeptide may be produced by standard protein expression techniques e.g. in *E. coli*. Purification of said polypeptide after its expression is preferably done, notably removal of nucleic acids coding for said polypeptide. Said polypeptide may be applied to a plant e.g. by spraying said plant with a liquid composition, preferably an aqueous solution, containing said polypeptide. Preferably, measures are taken to facilitate entering of said polypeptide into cells of a plant, notably measures that allow crossing of the plant cell wall and/or the outer plant layer. An example of such measures is slight wounding of parts of the plant surface e.g. by mechanical scratching. Another example is the use of cellulose-degrading enzymes to weaken or perforate the plant cell wall.

In an important embodiment of the invention, said external signal is a polypeptide and the application of said polypeptide does not involve the introduction of nucleic acids that code for said polypeptide or a functional part of said polypeptide into cells of said multi-cellular organism. A functional part of said polypeptide is a part that is capable of causing expression of said control protein according to step (b) of the method of the invention. In this embodiment, the multi-cellular organism is not endowed with genetic material coding for said polypeptide. Most preferably, the multi-cellular organism is not endowed in the method of the invention with (A) genetic material coding for said external signal and (B) with genetic material necessary for said cellular process of interest. Thus, these two types of genetic material (A) and (B) cannot be inherited together by said organism or be spread in the environment, notably to other organisms. In this embodiment, said polypeptide is preferably directly applied to cells of said organism. Direct application means application of said polypeptide such that no nucleic acids encoding said polypeptide or functional parts thereof are contained in a composition used in step (b) to apply said polypeptide. This may be achieved e.g. by particle bombardement or by application of a composition (e.g. a solution or suspension, or a cell-free composition) to said multi-cellular organism, whereby said composition contains said polypeptide but no nucleic acids coding for said polypeptide or a functional part thereof.

Alternatively, a composition containing said polypeptide and nucleic acids coding therefore may be applied to said multi-cellular organism, provided said nucleic acids coding for said polypeptide cannot enter cells of said organism. This may e.g. be achieved using a pathogenic microorganism that has a system of delivery of a polypeptide into a host cell. Said polypeptide may by expressibly encoded in nucleic acids of said pathogenic microorganism, such that said polypeptide can be delivered into a cell of said multi-cellular organism. A preferred example of such a pathogenic microorganism is a virulent or non-virulent *Agrobacterium*, whereby said polypeptide is not encoded in the T-DNA of a Ti-plasmid, preferably said polypeptide is not encoded on a Ti-plasmid of the *Agrobacterium* employed. Further examples of phyto-pathogenic microorganisms are *Bordetella, Erwinia, Pseudomonas, Xanthomonas, Yersinia*, the secretion systems of which may be used for the present invention. Examples for the use of the *Yersinia* type-III secretion system can be found in WO9952563. However, direct application of said polypeptide as described above is preferred.

Said externally applied signal causes expression of said control protein in cells that contain said heterologous nucleic acid and that were reached by said externally applied signal (primary expression of said control protein). Said heterologous nucleic acid of the invention has to be engineered such that said signal can cause expression of said control protein from said heterologous nucleic acid. There are numerous possibilities known in the art for achieving expression of the control protein in response to the external signal of the invention. Inducible promoters as described in the introduction of this specification may for example be used. In the case of a polypeptide as said external signal, said polypeptide may have an enzymatic activity rendering said heterologous nucleic acid expressible. Examples of such enzymatic activities are activities of site-specific recombinases, flippases, resolvases, integrases, transposases, polymerases etc. Further details of such possibilities including binding activities are given below.

Said control protein of the invention is capable of leaving cells of its primary expression and entering other cells of said multi-cellular organism or a part thereof (spreading of said control protein). In the case of plants, said leaving a cell and entering other cells preferably comprises cell-to-cell-movement or systemic movement in said plant or a part thereof. Said control protein preferably contains a protein portion enabling said leaving a cell and entering other cells. Said protein portion may be a domain of a viral movement protein or of a viral coat protein. Further, said protein portion may be a plant or animal transcription factor, or a domain of a plant or animal transcription factor capable of cell-toll or systemic movement. Further, said protein portion may be a plant or animal peptide intercellular messenger, or a domain of a plant or an animal peptide intercellular messenger. Moreover, said protein portion may be an artificial peptide capable of enabling cell-to-cell or systemic movement. Preferably, said protein portion is or comprises a viral movement protein or viral coat protein, or a domain of a viral movement or coat protein e.g. a tobamoviral movement or coat protein.

When the control protein of the invention enters other cells of the multi-cellular organism, said control protein is capable of controlling, notably inducing, expression of additional copies of said control protein in these cells. Thus, the method of the invention allows to amplify and propagate the signal applied externally within said multi-cellular organism. There are many ways how said control protein can be made to control its own expression from said heterologous nucleic acid. Said control protein may comprise a segment having a binding activity to said heterologous nucleic acid encoding said control protein. Said binding activity may trigger expression of said control protein. Said segment may act as a transcription factor inducing transcription of said hetereologous nucleic acid. Preferably, said control protein has a segment having an enzymatic activity capable of triggering expression of said control protein. Examples of such activities are activities of a site specific recombinase, flippase, resolvase, integrase, polymerase, or a transposase. Said enzymatic activity may modify said heterologous nucleic acid leading to expression of said control protein. Further, said segment may be a DNA-dependent RNA polymerase that acts on a promoter of said heterologous nucleic acid, whereby said promoter is not recognized by native polymerases of said multi-cellular organism. Examples of such promoter-polymerase systems are bacterial, viral, or bacteriophage promoter-polymerase systems like the T7 promoter-T7 polymerase.

Preferably, a binding or enzymatic activity of said control protein used to cause expression of said control protein may be of the same type as the binding or enzymatic activity of said polypeptide used as an external signal. More preferably, if said polypeptide is used as external signal, the same type of enzymatic activity is used for said polypeptide to cause expression of said control protein and for said control protein to cause its own expression.

Apart from the capability of controlling its own expression, the control protein of the invention has the capability of controlling a cellular process of interest. Said controlling may comprise enhancing and suppressing a cellular process of interest. Preferably, controlling means switching on or switching off a cellular process of Interest. Most preferably, controlling means switching on a cellular process. For being capable of controlling said cellular process of interest, said control protein (protein switch) may have a segment that is capable of controlling said cellular process. Said segment may have a binding activity or an enzymatic activity that controls a nucleic acid (e.g. said additional heterologous nucleic acid described below) necessary for said cellular process of interest. In the method of the invention, said controlling of said cellular process (iii) may be achieved analogously to said causing expression of said control protein (ii). For this purpose, said control protein may have a segment for controlling said cellular process (iii) and a segment for causing said expression of said control protein (ii), whereby the control mechanisms of said two segments may be different. Preferably, the two control mechanisms are similar or identical, wherein one segment of said control protein may be sufficient for controlling (iii) and (ii). Thus, in a preferred design, said control protein of the invention contains at least one segment for controlling (ii) and (iii) and a portion endowing said control protein with the capability of leaving a cell and entering other cells of said multi-cellular organism.

Said cellular process of interest typically requires the presence of an additional heterologous nucleic acid in cells of said multi-cellular organism where said cellular process is to be controlled. Said additional heterologous nucleic acid may be present in all cells or in a fraction of cells of said multi-cellular organism. It may be stably incorporated in nuclear or organellar genomes of cells of said organism. What has been said regarding said heterologous nucleic acid of the invention generally applies also to said additional heterologous nucleic acid. With respect to said cellular process of the invention, there are no particular limitations and the invention is of very broad applicability. Important examples of such cellular processes are the production of an RNA and/or a polypeptide of interest from said additional heterologous nucleic acid or the formation of an expressible operon from said additional heterologous nucleic acid or from an RNA expression product of said additional heterologous nucleic acid. A very important example of a cellular process is the formation of an expressible amplicon from said additional heterologous nucleic acid or from an RNA expression product of said additional heterologous nucleic. Said amplicon is capable of amplifying within cells of its activation or formation. Further, said amplicon may be capable of cell-to-cell or systemic movement in the multi-cellular organism of the invention. Thus, a function of said amplicon may be amplified to a very high level triggered by said protein switch. The amplification properties of said protein switch and said amplicon may behave synergistically, thus allowing an extremely strong cellular process of interest (e.g. extremely strong expression of a protein of interest from said amplicon).

A sequence portion of said additional heterologous nucleic acid may be operably linkable to a transcription promoter by the action of said control protein, which allows to switch on expression of a protein of interest or transcription of an RNA-viral amplicon from said additional heterologous nucleic acid, e.g. by operably linking a sequence encoding said protein of interest or an RNA amplicon with a promoter. There are several ways of reducing this embodiment to practice. One option is to separate, in said additional heterologous nucleic acid, the sequence encoding an RNA amplicon and a promoter by a sequence block that precludes an operable linkage therebetween. Said sequence block may be flanked by recombination sites such that said block can be cut out by a recombinase recognizing said recombination sites. Thereby, operable linkage for transcription of the sequence encoding an RNA amplicon can be established and expression may be switched on. Another option is to have a portion of a sequence necessary for transcription (e.g. a promoter or promoter portion) in flipped orientation and flanked by recombination sites. Providing a suitable recombinase may flip said sequence portion back in correct orientation, whereby an operable linkage can be established.

In a further embodiment of this invention, the protein expressed from said heterologous nucleic acid and said polypeptide used as externally applied switch jointly generate a predetermined function leading to switching on said cellular process of interest only when the protein and said polypeptide are jointly present. The protein expressed from said heterologous nucleic acid may e.g. be constitutively expressed, whereby the process of interest can be switched by applying said polypeptide. Alternatively, the protein expressed from said heterologous nucleic acid may be under the control of a regulated promoter (e.g. a chemically inducible promoter), which allows a "double" control of the process of interest, namely by induction of the regulated promoter and by applying said polypeptide. Preferably, said protein and said polypeptide jointly generate said predetermined function (e.g. an enzymatic activity as those mentioned above) by intein-mediated trans-splicing or by intein-mediated affinity interaction. Said predetermined function may then switch on the cellular process of the invention. Said predetermined function may e.g. be a binding activity or an enzymatic activity that may act on said additional heterologous nucleic acid similar as described above for said control protein. An important advantage of this embodiment is that the plant provided in step (a) that is genetically-modified with a heterologous nucleic acid does not contain all components required for switching on said cellular process of the invention. Thus, said plant cannot transfer genetic information for a functional cellular process or interest to progeny or to other organisms.

The cellular process according to the invention may comprise a whole biochemical cascade of interest like a multi-step biosynthetic pathway in cells of the organism. The cellular process or biochemical cascade of interest is not operable in the multicellular organism prior to exposure to the externally applied signal. The cellular process of the invention provides control over a cellular process or biochemical cascade of interest with a hitherto unattainable technical precision and environmental safety. Thereby novel applications in biotechnology in general, specifically in plant biotechnology, are available for solving problems which cannot be solved by conventional technologies involving basal transgene expression activity in a plant, particularly when producing toxic substances or biodegradable polymers. Moreover, the precise control according to the invention allows to grow a transgenic plant to a desired stage where, for example, the plant is best suited for performing the biochemical process or cascade of interest without burdening the plant with a basal expression activity slowing down the growth of the plant. Once the plant is ready for efficiently performing the cellular process or cascade of interest, the process or cascade of interest may be switched on and performed with high efficiency. Accordingly, the method of the invention allows to safely decouple the growth phase and the production phase of a multicellular organism, specifically a transgenic plant. Moreover, it is possible to design multi-component systems for multiple cellular processes or biochemical cascades of interest, whereby one or more desired processes or cascades can be selectively switched on.

PREFERRED EMBODIMENTS OF THE INVENTION

A method of controlling a cellular process of interest in a genetically-modified multi-cellular organism or a part thereof, comprising the following steps:
(a) providing a multi-cellular organism or a part thereof, whereby cells of said multi-cellular organism contain a heterologous nucleic acid,
(b) causing expression of a control protein from said heterologous nucleic acid in at least some of said cells,
wherein said control protein is capable of
(i) leaving a cell and entering other cells of said multi-cellular organism or a part thereof,
(ii) causing expression of said control protein in cells containing said heterologous nucleic acid, and
(iii) controlling said cellular process of interest.

A method of controlling a cellular process of interest in a genetically-modified multi-cellular plant or a part thereof, comprising the following steps:
(a) providing a multi-cellular plant, whereby cells of said multi-cellular plant contain a heterologous nucleic acid,
(b) causing expression of a control protein from said heterologous nucleic acid in at least some of said cells,
wherein said control protein is capable of
(i) leaving a cell and entering other cells of said multi-cellular plant,
(ii) causing expression of said control protein in cells containing said heterologous nucleic acid, and
(iii) controlling said cellular process of interest.

A method of controlling a cellular process of interest in a genetically-modified multi-cellular plant or a part thereof, comprising the following steps:
(a) providing a multi-cellular plant, whereby cells of said multi-cellular plant contain a heterologous nucleic acid,
(b) causing expression of a control protein from said heterologous nucleic acid in at least some of said cells by an externally and directly applied polypeptide,
wherein said control protein is capable of
(i) leaving a cell and entering other cells of said multi-cellular plant, (ii) causing expression of said control protein in cells containing said heterologous nucleic acid, and
(iii) switching on said cellular process of interest.

(A) depicts a heterologous nucleic acid encoding PS:TP and an additional heterologous nucleic acid hNA. No external signal is applied, thus the protein switch is not expressed.

(B) an external signal is applied causing expression of the protein-switch PS:TP. The protein switch can control a cellular process by acting on hNA in the cell of its expression. Further, the protein switch can leave the cell that was triggered by said external signal and enter other cells. In other cells, the protein switch can induce its own expression and also control a cellular process by acting on hNA.

(C) depicts a heterologous nucleic acid encoding two protein switches: PS1 and PS2. Expression of PS1 is caused by an externally applied signal, leading to PS1:TP. As above, PS1:TP can spread to other cells and activate expression of PS2. PS2 in turn can control a cellular process by acting on hNA, which can be transiently present in the cell or stably integrated into the nuclear or organellar genome. For such a purpose, PS2 can be fused to the appropriate targeting signal/transit peptide in order to reach the hNA located in organelles like chloroplasts.

Figure 3:
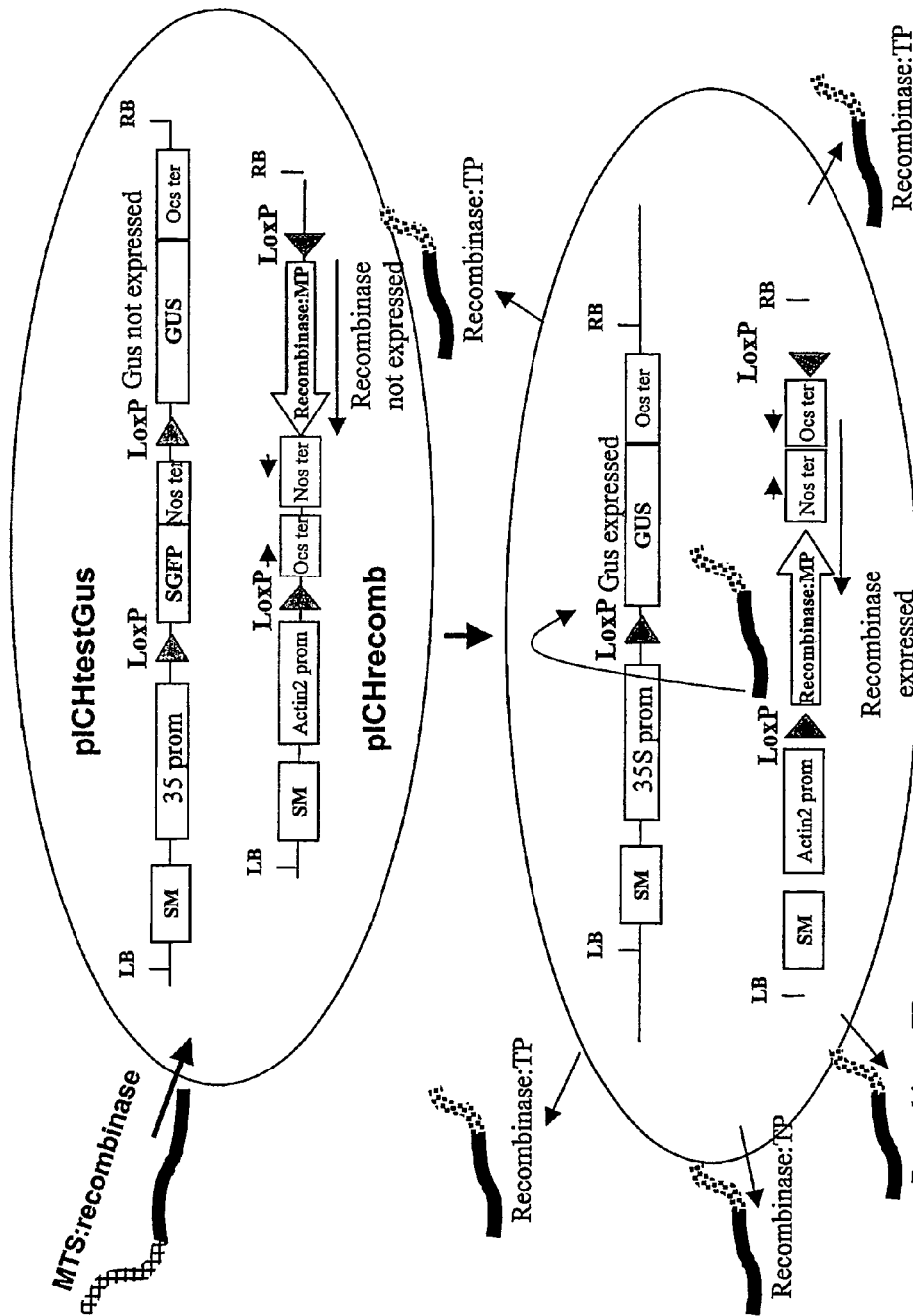

FIG. 3 is a schematic presentation of the constructs pICH-testGus and pICHrecomb designed for triggering the expression of the gene of interest (GUS) as the result of a site-specific recombination event. Said recombination events can be caused by an externally applied recombinase as well as by an intracellular recombinase capable of cell-to cell movement.

Figure 4:
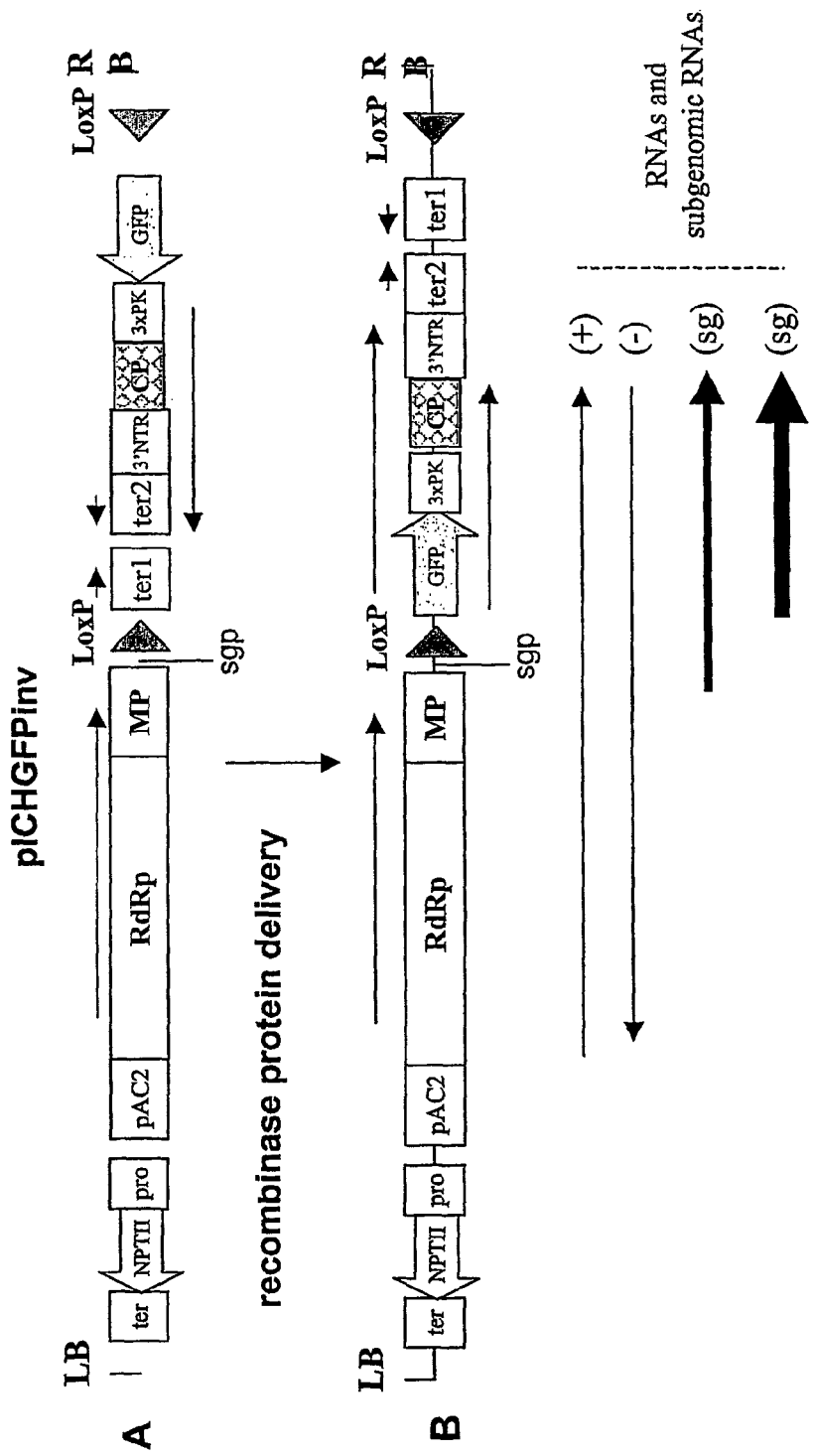

FIG. 4 depicts in (A) the construct pICHGFPinv containing a non-functional TMV-based provector and in (B) a functional derivative of said construct resulting from integrase-mediated recombination. Arrows at the bottom indicate RNAs and subgenomic (sg) RNAs including their orientation that can be formed from the construct shown in (B). sgp stands for subgenomic promoter.

Figure 5:
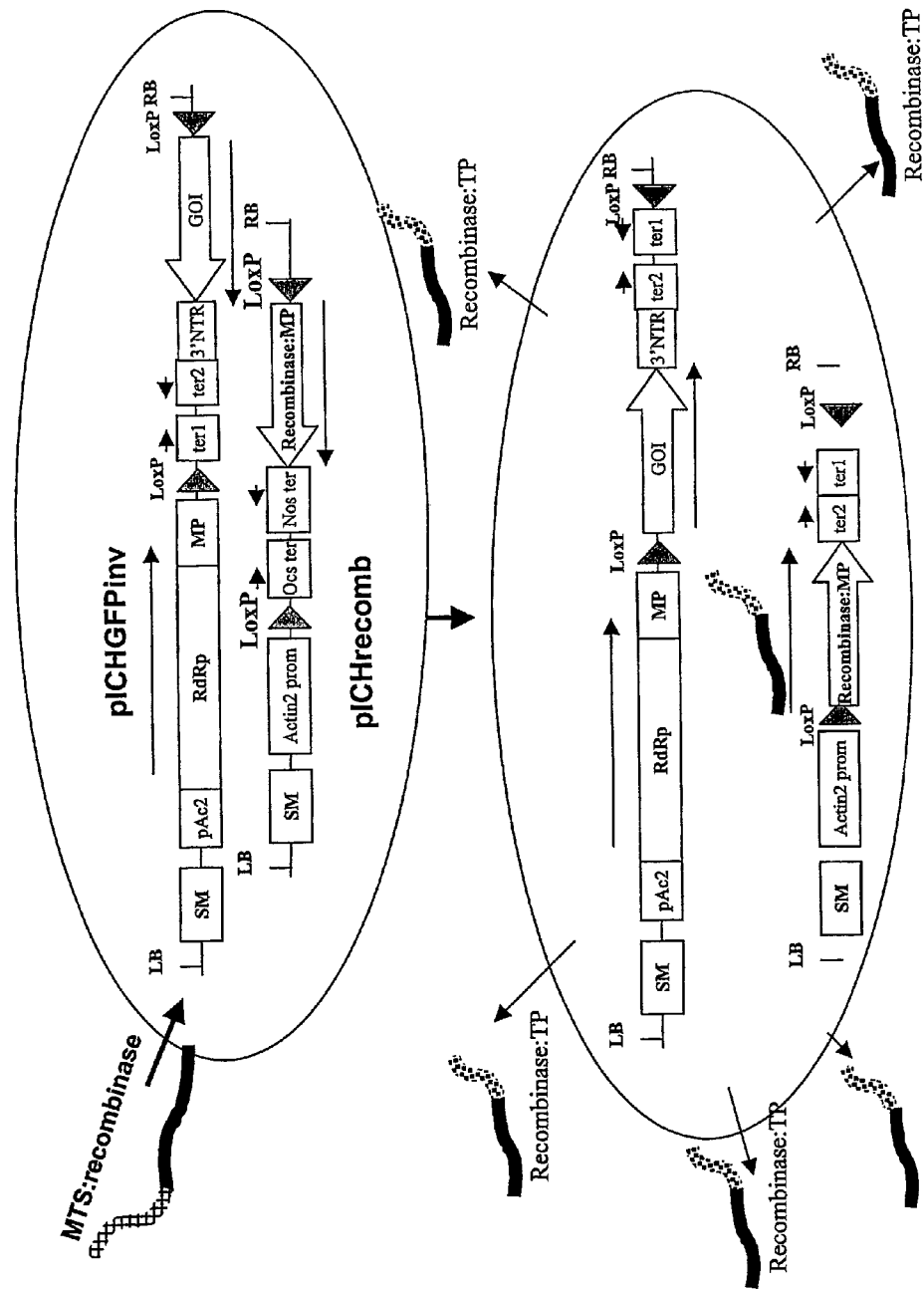

FIG. 5 depicts an experimental scheme wherein a cell-permeable polypeptide as external signal (MTS:recombinase) triggers recombination events within targeted cells leading to the synthesis of a protein-switch capable of intercellular trafficking (recombinase:TP). The intracellular protein-switch can further trigger recombination events leading to rearrangement of a plant virus-based pro-vector resulting in expression of a gene of interest (GOI). MTS: membrane translocating sequence; TP: protein capable of intercellular trafficking; SM: selectable marker, RS: recombination site recognized by site-specific DNA recombinase/integrase; ter1 and ter2: transcription termination regions; PROM: promoter active in plants; RdRp: viral RNA-dependent RNA polymerase; MP: movement protein; 3'NTR: 3' non-translated region of plant RNA virus. Arrows show the orientation of coding and regulatory sequences.

Figure 6:
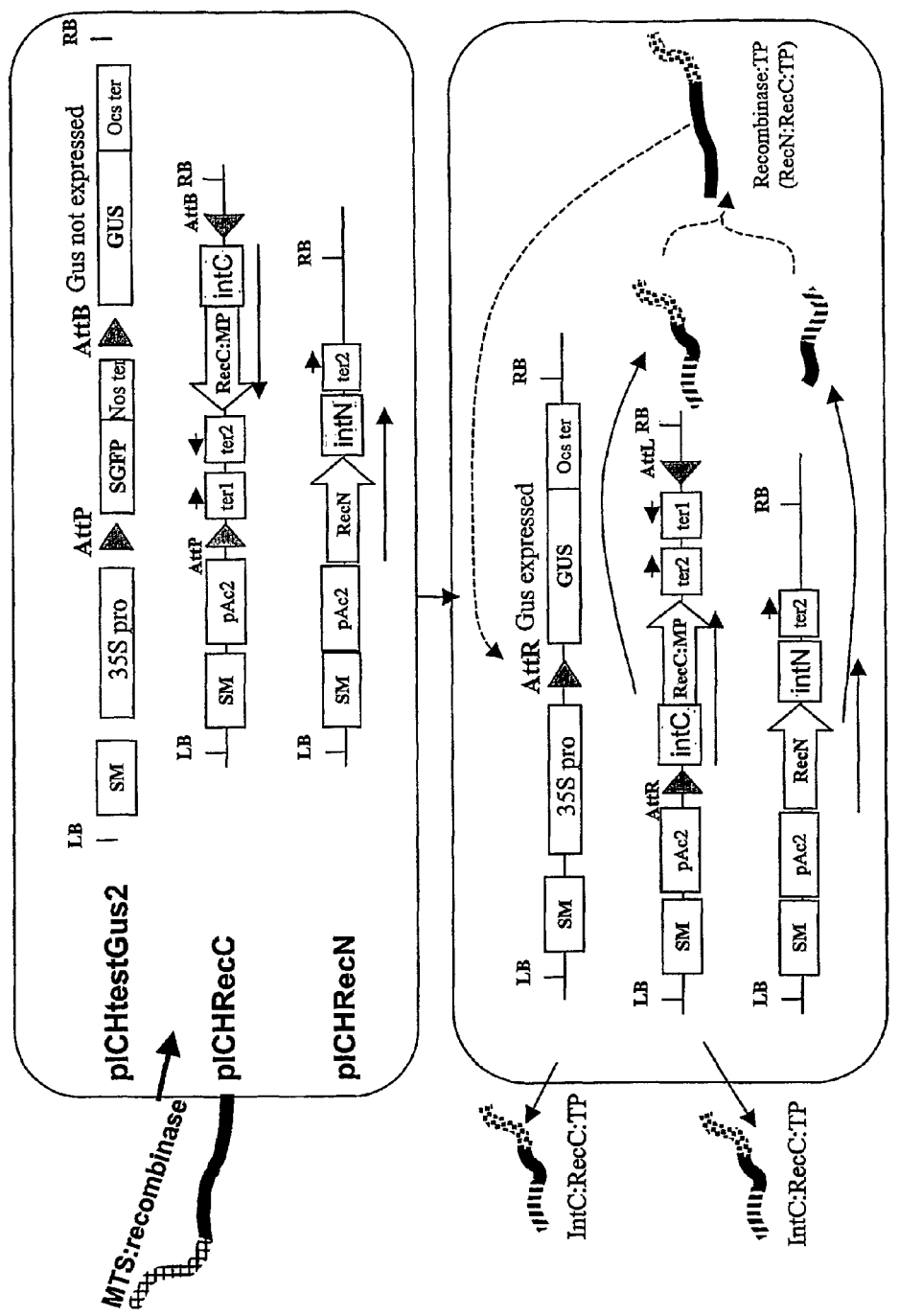

FIG. 6 depicts an experimental scheme for the use of a protein-switch fragment capable of cell-to-cell movement.

MTS:recombinase—externally applied recombinase-switch fused to a membrane translocating signal peptide (MTS); RecN—N-terminal end of recombinase followed by intein fragment (intN) as translational fusion; iintC—intein fragment capable of interacting with intN fragment and followed by c-terminal end of recombinase fused to movement protein (RecC:MP).

FIG. 7 (A, B) depicts schematically constructs pICH11992, pICH11877, and pICH12131. P35S—CaMV 35S promoter; Tnos—transcription termination signal of nopalin synthase; Pnos—transcription promoter of nopalin synthase gene; Tocs transcription termination signal of octopin synthase; MP—movement protein of Tobacco Mosaic Virus (TMV); cre-5'—5' part of cre recombinase coding sequence; cre-3'—3' part of cre recombinase coding sequence.

DETAILED DESCRIPTION OF THE INVENTION

Figure 1:
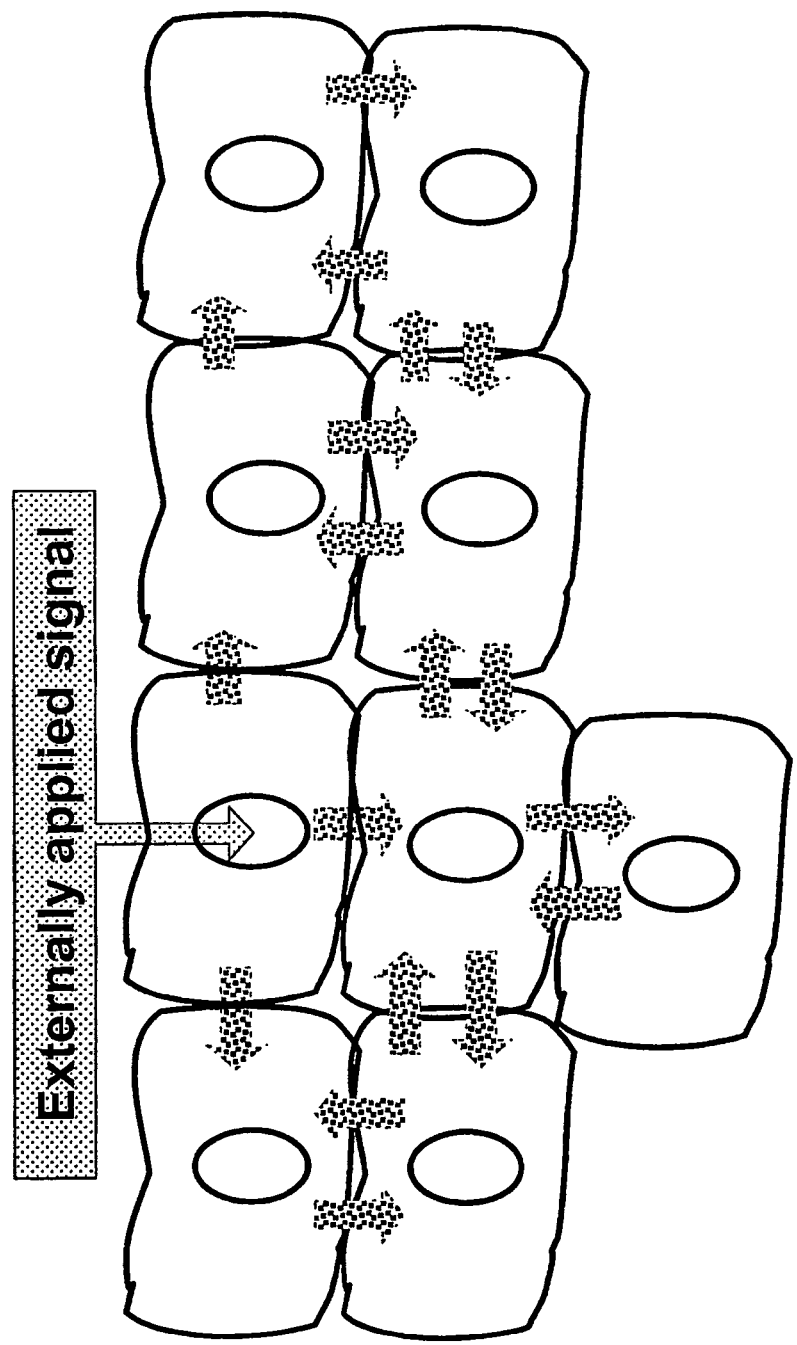
FIG. 1 is a schematic representation of a method according to the invention.
Figure 2:
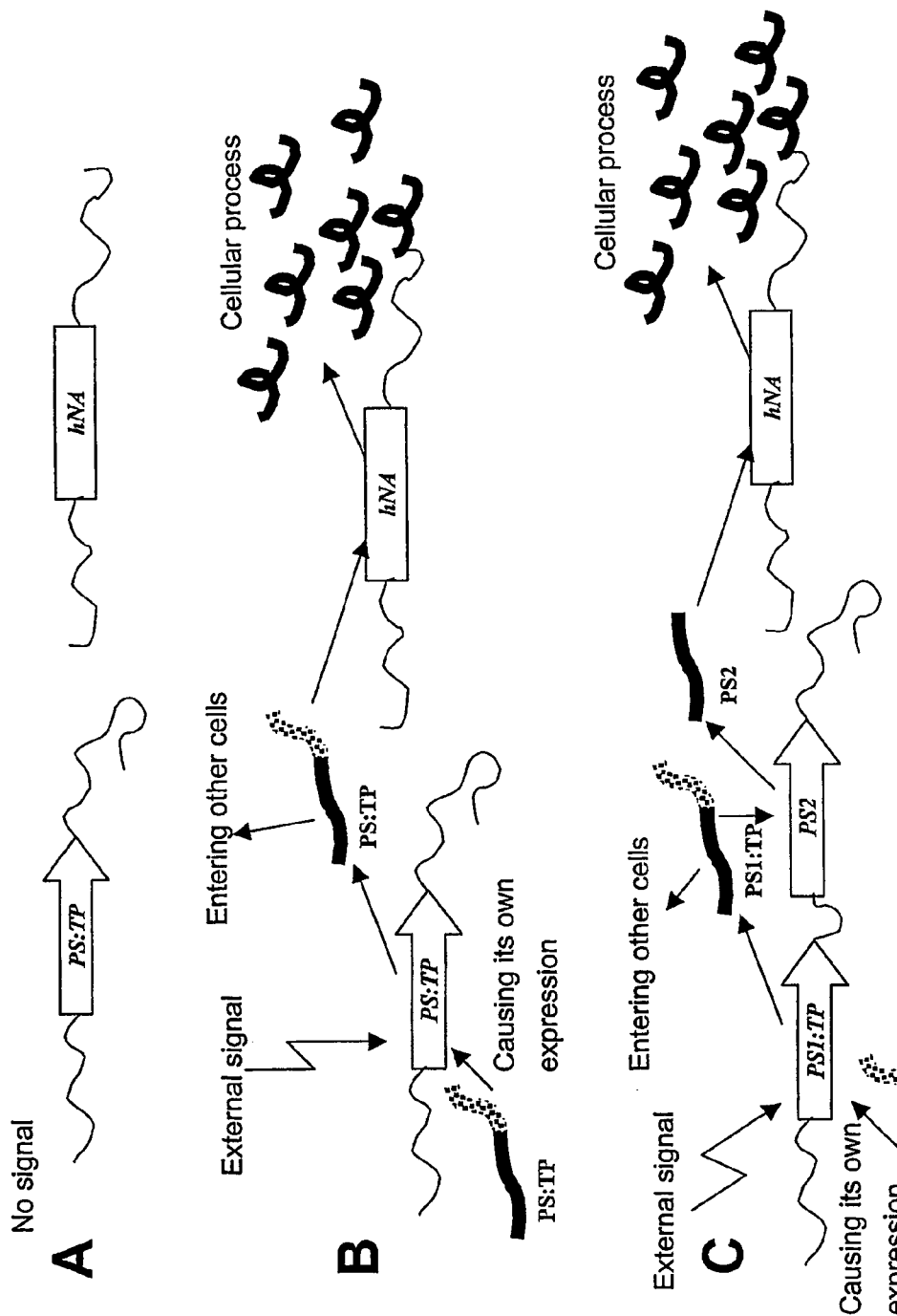
FIG. 2 is general representation of mechanisms controlling a cellular process of interest via a protein-switch that is capable of intercellular trafficking and causing its own expression in other cells. PS stands for protein switch, TP stands for a trafficking protein capable of intercellular trafficking, PS:TP stands for a PS-TP fusion protein, hNA stands for an additional heterologous nucleic acid.

The basis of this invention is the use of a control protein capable of leaving cells and entering other cells of a multi-cellular organism. Said control protein is capable of causing its own expression and, in addition, it is capable of controlling a cellular process of interest different from its own expression. The general principle and a schematic representation of the method according to the invention are shown in FIGS. 1 and 2, respectively.

Choice of Control Protein for "Switch" Function

There are countless numbers of cellular processes of interest which can, preferably irreversibly, be triggered by said control protein of the invention (protein switch). The protein switch can e.g. control the expression of a transgene of interest in many different ways, whereby these ways may also be used for the switching function of said polypeptide used as external trigger. For example, it can trigger DNA recombination or transcription, RNA processing or translation, protein post-translational modifications etc. In addition, the protein switch can be activated by said polypeptide upon delivery into the plant cell and after that be able to function as a switch. Obviously, the choice of the protein switch depends on the design/choice of the cellular process to be controlled in said multi-cellular organism, notably in said plant. Said cellular process may be controlled, notably switched on, by nucleic acid rearrangement or modification in cells wherein said control protein is present or in cells that are invaded by said control protein. In such case, the protein switch may comprise a DNA or RNA modifying enzyme like a site-specific endonuclease, a replicase, a recombinase, a methylase, an integrase, a transposase, a polymerase etc.

There are numerous reactions that affect RNA molecules that may be used as efficient triggering device for the cellular process according to the present invention. These include, inter alia, reactions such as RNA replication, reverse transcription, editing, silencing, or translation. There is abundant prior art describing in detail how, for example, a site-specific recombinase, integrase or transposase can trigger a process of interest by DNA excision, inversion or insertion in cells, notably In plant cells (Zuo, Moller &Chua, 2001, *Nat. Biotech.*, 19, 157-161; Hoff, Schnorr & Mundy, 2001, *Plant Mol. Biol.*, 45, 41-49; U.S. Pat. No. 5,225,341; WO9911807; WO9925855; U.S. Pat. No. 5,925,808; U.S. Pat. No. 6,110, 736 WO0140492; WO 0136595). Site-specific recombinases/integrases from bacteriophages and yeasts are widely used for manipulating DNA in vitro and in plants and animals. Preferred recombinases-recombination sites for the use in this invention are the following: Cre recombinase-LoxP recombination site, FLP recombinase-FRT recombination sites, R recombinase-RS recombination sites, phage C31 integrase recognising attP/attB sites etc. Transposons are widely used for the discovery of gene function in plants. Preferred transposon systems for use in the present invention include Ac/Ds, En/Spm, transposons belonging to the "mariner" family, etc.

Heterologous transcription factors and RNA polymerases may also be used in a protein switch according to the invention. For example, the delivery of T7 polymerase into cells of a plant carrying a transgene under the control of the T7 promoter may induce the expression of such a transgene.

The expression of a plant transgene (e.g. the additional heterologous nucleic acid of the invention) that is under control of a bacteriophage promoter (e.g. T3, T7, SP6, K11) with the corresponding DNA/RNA polymerase delivered into cells of a plant may be another efficient approach for the development of protein switches contemplated in this invention. Another useful approach may be the use of heterologous or chimaeric or other artificial promoters which require heterologous or engineered transcription factors for their activation. Heterologous transcription factors also can be used in order to induce expression of the transgene of interest under control of said transcription factor-recognisible promoter. Examples of such transcription factors include the yeast metalloresponsive ACE1 transcription factor binding specific sequences in the yeast MT (metallothionein) promoter (Mett et al., 1993, *Proc. Natl. Acad. Sci.*, 90, 4567-4571), different chimaeric transcription factors having a sequence-specific DNA-binding domain and an activation domain like a transcription factor having a fusion six-zink finger protein 2C7 and herpes simplex virus VP16 transcription factor activation domain (Ordiz, Barbas & Beachy, 2002, *Proc. Natl. Acad. Sci. USA*, 99, 13290-13295), transcription factor having a full length 434 repressor and the C-terminal 80 amino acids of VP16 transcriptional activator (Wilde et al., 1994, *Plant Mol. Biol.*, 24, 381-388), transcription factor used in steroid-inducible systems (Aoyama & Chua, 1997, *Plant J.*, 11, 605-412; McNellis et al., 1998, *Plant J.*, 14, 247-257; U.S. Pat. No. 0,606,3985) or a tetracycline-inducible system (Weinmann et al, 1994, *Plant J.*, 5, 559-569). In some cases, the existing inducible systems for transgene expression may be used. Alternatively, heterologous transcription factors may be modified such that no activating ligand-inducer will be required to drive the transcription factor into the active state. Chimaeric transcription factors would be of advantage for the use in this invention, as they allow to combine highly sequence-specific DNA binding domains and highly efficient activation domains, thus allowing a maximum desired effect after delivery of such a factor into the plant cell.

Another protein switch contemplated under the invention may rely on posttranslational modification of one or more additional heterologous nucleic acid(s). There are many possible implementations of such protein switches that could operate by controlling steps such as polypeptide folding, oligomer formation, removal of targeting signals, conversion of a pro-enzyme into an enzyme, blocking enzymatic activity, etc. For example, delivery of a site-specific protease into cells of a multi-cellular organism may trigger a cellular process of interest if a genetically-engineered host specifically cleaves a pro-enzyme, thus converting it into an active enzyme, if a product is targeted to a particular cellular compartment because of the host's ability to cleave or modify a targeting motif, or if a product is specifically mobilized due to the removal of a specific binding sequence. Cleavage of a translational fusion protein can be achieved via a peptide sequence recognized by a viral site-specific protease or via a catalytic peptide (Dolja et al., 1992, *Proc. Natl. Acad. Sci. USA*, 89 10208-10212; Gopinath et al., 2000, *Virology*, 267, 159-173; U.S. Pat. No. 5,162,601; U.S. Pat. No. 5,766,885; U.S. Pat. No. 5,491,076). Other examples of site-specific proteases applicable to this invention are mammalian enterokinases, for example, human enterokinase light chain which recognizes the sequence DDDK-I (SEQ ID NO:1) (Kitamoto et al., 1994, *Prtoc. Natl. Acad. Sci.*, 91, 7588-7592), and specifically cleaves Lys-Ile bonds; viral proteases, like Hc-Pro (Carrington J C & Herndon K L, 1992, *Virology*, 187, 308-315) which catalyses proteolysis between the Gly-Gly dipeptide but requires 4 amino acids for the recognition of the cleavage site; site-specific protease of Semliki Forest Virus (Vasiljeva et al., 2001, *J Biol. Chem.*, 276, 30786-30793); and proteases involved in polyubiquitin processing, ubiquitin-carboxy-terminal hydrolases (Osava et al., 2001, *Biochem Biophys Res Commun.*, 283, 627-633).

Choice of Externally Applied Signal

Any abiotic or biotic factor can be used as externally applied signal in order to cause expression of said control protein (said protein switch) within the cells of said multi-cellular organism. Said protein-switch may e.g. be under the control of an inducible promoter that is triggered e.g. by a chemical agent, environmental change, pathogen attack. Said promoter can drive the expression of said protein-switch that is capable of intercellular trafficking and switching on the cellular processes and/or biochemical cascade in cells it enters, thus providing for even expression of said process and or cascade in affected cells of said plants or parts thereof. Examples of such inducible systems are described above.

A preferred choice of externally applying said signal is the direct or bacterium-mediated delivery of a polypeptide into cells of said multi-cellular organism, whereby said polypeptide is capable of causing expression of said control protein. Alternatively, said polypeptide may be transiently expressed in said plant cell or group of cells of said genetically-modified multi-cellular organism. Unlike, e.g. inducible promoters, said protein-switch is highly specific and can provide for tight control of the expression of a cellular process of interest. Depending on construct design, said polypeptide can trigger expression of said protein switch after the delivery into a plant cell or group of cells. The most preferred and biologically safe way of delivering said polypeptide without delivering nucleic acids encoding said polypeptide into the plant cell or group of cells are described in the following.

Delivery of Said Polypeptide or of a Fragment Thereof into Cells of a Multi-Cellular Plant a) Direct Delivery Different methods can be used for the direct delivery of said polypeptide into cells of said multi-cellular plant organism. Among the simplest ones is the direct delivery with the help of mechanical interaction with plant tissue. For example, microprojectile bombardment of polypeptide-coated particles can deliver said polypeptide into the plant cell. The protocol can be similar to those described for DNA delivery in plant transformation protocols (U.S. Pat. No. 0,510,0792; EP 00444882B1; EP 00434616B1). However, instead of DNA, said polypeptide may be used for coating the particles. There is a description of a biolistic process that uses particle coating methods which are reasonably gentle for preserving the activity of said polypeptide (Sanford, Smith & Russell, 1993, *Methods in Enzymol.*, 217, 483-509). In principle, other plant transformation methods can also be used e.g. microinjection (WO 09209696; WO 09400583A1; EP 175966B1), or liposome-mediated delivery (for review see: Fraley & Papahadiopoulos, 1982, *Curr. Top Microbiol. Immunol.*, 96, 171-191).

B) Use of Membrane Translocation Amino Acid Sequences

The polypeptide of interest can be applied externally to target cells of said plant using a covalent fusion or non-covalent interaction with a membrane translocating sequence. Many examples of membrane translocating sequences (MTS), natural and synthetic, are known in the art. They are widely used as fusions with peptide drugs and therapeutic proteins in order to increase their cell membrane permeability. An MTS may be a simple amino acid repeat, for example a cationic peptide containing eleven arginines RRRRRRRRRRR (SEQ ID NO:2) (Matsushita et al., 2001, *J. Neurosci.*, 21, 6000-6007). Another cationic MTS is a 27 amino acid long transportan (GWTLNSAGYL LGKINLKALA ALAKKIL; SEQ ID NO:3) (Pooga et al., 1998, *FASEB J*, 12, 67-77). It is very likely that such peptides, for their penetration of the cell, exploit the asymmetry of the cellular plasma membrane where the lipid monolayer facing the cytoplasm contains anionic phospholipids (Buckland & Wilton, 2000, *Biochim. Biophys. Acta/Mol. Cell. Biol. Of Lipids*, 1483, 199-216). Certain proteins also contain subunits that enable their active translocation across the plasma membrane into cells. To such domains belongs the basic domain of HIV-1 Tat$_{49-57}$ (RKKRRQRRR; SEQ ID NO:4) (Wender et al., 2000, *Proc. Natl. Acad. Sci. USA*, 97, 13003-13008), Antennapedia$_{43-58}$ (RQIKIWFQNR RMKWKK; SEQ ID NO:5) (Derossi et al., 1994, *J. Biol. Chem.*, 269, 10444-10450), the Kaposi Fibroblast Growth Factor MTS (AAVALLPAVL LALLAP; SEQ ID NO:6) (Lin et al., 1995, *J. Biol. Chem.*, 270, 14255-14258); the VP22 MTS (Bennet, Dulby & Guy, 2002, *Nat. Biotechnol.*, 20, 20; Lai et al., 2000, *Proc. Natl. Acad. Sci. USA*, 97, 11297-302); homeodomains from the *Drosophila melanogaster* Fushi-tarazu and Engrailed proteins (Han et al., 2000, *Mol Cells* 10, 728-732). It was shown that all these positively charged MTSs are able to achieve cell entry by themselves and as fusions with other proteins like GFP (Zhao et al., 2001, *J. Immunol. Methods*, 254, 137-145; Han et al., 2000, *Mol Cells*, 10, 728-732), Cre recombinase (Peitz et al., 2002, *Proc. Natl. Acad. Sci. USA*, 4489-4494) in an energy-independent manner. However, the fusion is not necessarily required for protein transport into the cell. A 21-residue peptide carrier Pep-1 was designed (KETWWETWWTEWSQPKKKRKV; SEQ ID NO:7) which is able to form complexes by means of non-covalent hydrophobic interactions with different types of proteins, like GFP, b-Gal, or full-length specific antibodies. These complexes are able to efficiently penetrate cell membranes (Morris et al., 2001, *Nature Biotechnol.*, 19 1173-1176). The list of MTS can be continued and, in general, any synthetic or naturally occurring arginine-rich peptide can serve for practicing this invention (Futaki et al., 2001, *J. Biol. Chem.*, 276, 5836-5840).

As there is no essential structural difference between plant and animal cell membranes affecting their general architecture and physico-chemical properties, said fusions of MTS with a polypeptide of interest can also be efficiently used for penetrating plant cells. However, unlike animal cells, plant cells possess a tough cell wall (Varner & Linn, 1989, *Cell*, 56, 231-239; Minorsky, 2002, *Plant Physiol.*, 128, 345-53). This obstacle can be overcome by using simple techniques. For example, injection of a (e.g. crude) protein extract containing said polypeptide having a MTS into a plant apoplast facilitates translocation of said polypeptide into the plant cells. Another approach to overcome the cell wall and to reach the cell membrane of plant cells can be the application of cellulytic enzymes many of which are commercially available. Once added to a composition containing said polypeptide, said enzymes help to remove or weaken the cell wall, but will leave the cell membrane intact and exposed for penetration by said polypeptide containing said MTS. Said cellulytic enzymes from bacteria and molds have been commercially available at industrial scale for a long time and are widely used (e.g. "Onozuka" R-10 enzyme preparation of *Trichoderma harzianum*, etc) in plant cell tissue culture for obtaining plant protoplasts (Sidorov & Gleba, 1979, *Tsitologia*, 21, 441-446; Gleba & Gleba, 1978, *Tsitol Genet.*, 12, 458-469; Ghosh et al., 1994, *J. Biotechnol.*, 32; 1-10; Boyer, Zaccomer & Haenni, 1993, *J. Gen. Virol.*, 74, 1911-1917; Hilbricht, Salamini & Bartels, 2002, Plant J., 31, 293-303). The approach of using cellulytic enzymes has potential for large scale applications of this invention. A mixture of cellulytic enzymes with a cell-permeable polypeptide can be sprayed over the genetically-modified plants or over parts thereof. Cellulases can make cell membranes accessible for membrane permeable polypeptides. Upon translocation into the cell, said polypeptide may trigger said cellular process of interest and the expression of said control protein within the plant.

C) Pathogen-Mediated Delivery of Said Polypeptide

Some plant pathogens have very efficient systems for delivering effector proteins into the plant cells. Many plant and animal pathogenic bacteria use specialized secretion systems to deliver effector proteins into the host cells. There are many descriptions in the literature of such secretory systems, for example the type III secretion system for gram-negative bacteria (Binet et al., 1997, *Gene*, 192, 7-11; Thanassi & Hultgren, 2000, *Curr. Opin. Cell Biol.*, 12, 420-430; Buttner & Bonas, 2002, *Trends Microbiol.*, 10, 186-192; Buttner & Bonas, 2003, Curr. Opin. Plant Biol., 6, 321-319) and the type II secretory system for proteobacteria (Sandkwist, 2001, *Mol. Microbiol.*, 40, 271-283). Multiple pathways of protein secretion from bacteria are described in the review of Thanassi and Hultgren (2000, *Curr. Opin. Cell Biol.*, 12, 420-430.

Type III secretion systems of different phytopathogenic bacteria were described with enough details to open the possibility of using said bacteria for delivery into the plant cell heterologous protein of interest. For example, the Hrp gene cluster (type III protein secretion) was cloned from *Erwinia chrysanthemi* (Ham et al., 1998, *Proc. Natl. Acad. Sci. USA*, 95, 10206-10211); *Pseudomonas syringae* secretion system is described with sufficient for using in this invention details (for review see Jin et al., 2003, *Microbes Infect.*, 5, 301-310); secretory system of *Xanthomonas campestis* is being intensively studied (Marois et al., 2002, *Mol. Plant Microbe Interact.*, 15, 637-646; Szurek et al., 2002, *Mol. Microbiol.*, 46, 13-23).

Plant pathogens (phytopathogens) as candidates for the delivery of the polypeptide into plant cells are however of limited value for the present invention, especially phytopathogens that cause substantial damage to host plants. As a preferred alternative, phytopathogens can be engineered such that they are able to transfer a heterologous protein of interest without causing any ill effect on the host plant. Further, non-pathogenic bacteria can be engineered such that they possess that part of the type III secretion system necessary for the delivery of a heterologous protein of interest into the plant cell, but not other parts that damage the host plant.

Some gram-negative bacteria, like *Agrobacterium tumefaciens* and *Agrobacterium rhizogenes*, are well studied and are widely used for introducing recombinant DNA into plant cells (Zambryski, 1988, *Annu Rev Genet.*, 22, 1-30; Hiei, Komari & Kubo, 1997, *Plant Mol Biol.*, 35, 205-18; Newell, 2000, *Mol. Biotechnol.*, 16, 53-65). They are able to deliver T-DNA into the nuclei of many plant species and the mechanism of such transport is reasonably well studied (Hooykaas & Beijersbergen, 1994, *Annu. Rev. Phytopathol*, 32, 157; Zupan & Zambryski, 1995, *Plant Physiol.*, 107, 1041-1047; Hansen & Chilton, 1996, *Proc Natl Acad Sci USA*, 93, 14978-1483). Among plant pathogens, *Agrobacteria* are best suited for the present invention. The publication of Hooykaas' group (2000, *Science*, 290, 979-982) demonstrates the possibility of *Agrobacterium*-mediated transfer of Cre recombinase as a heterologous protein into host cells. The transfer was achieved by using a translational fusion of Cre with virulence proteins or their parts involved in protein translocation into the plant cell during contact with *Agrobacterium*. Cre recombinase delivery was not coupled with transfer of DNA encoding said recombinase, but was efficient enough to trigger recombination events in engineered target cells. The process of bacterium-mediated polypeptide delivery into plant cells requires the availability of engineered bacterial cells carrying the gene of said polypeptide (WO0189283). Such a process Is efficient enough to trigger selectable changes in plant cells in cell culture, but has serious disadvantages that significantly restrict its applicability: Firstly, it does not provide control over transgene segregation, as the entire coding sequence for said polypeptide is present in the phytopathogenic bacteria. Secondly, it is not efficient enough to have practical applications with entire multi-cellular organisms like plants, as the changes triggered by said polypeptide are restricted to the cells having received said polypeptide.

Control Over Segregation of a Transgene Encoding the Protein Switch or Said Polypeptide For the above reasons, either a very efficient method of delivering said polypeptide as said external signal to each or most of the cells of the targeted plant or an efficient spread of said protein switch or the combination of both approaches is required. Further, to make the overall method safe, strict control over the heterologous nucleic acid encoding said protein-switch is required. This can be achieved either by using direct application of said polypeptide (e.g. treating plants with the solution containing said polypeptide), or by using bacterial delivery of said polypeptide, whereby one part of said polypeptide is supplied by bacteria and another part is encoded in cells of the targeted plant.

In order to address these issues it is proposed herein to use a "split genes" approach for controlling the segregation of a transgene encoding the protein switch. In this embodiment, an active protein-switch is assembled either by intein-mediated protein trans-splicing or by affinity interaction, e.g. of said externally applied polypeptide and a polypeptide produced in cells of said organism. This is an especially important issue for a phytopathogen-delivered protein switch or polypeptide. In this case, the protein-switch is preferably not encoded by a continuous DNA sequence and its use may be much better controlled. Importantly, this embodiment has an exceptional biological safety.

Intein-mediated trans-splicing of proteins with restoration of their activity is known in the prior art and is described in detail in many publications. Protein affinity interaction and/or trans-splicing can be achieved by using engineered inteins. Inteins were first identified as protein sequences embedded in-frame within protein precursor and excised during the protein maturation process (Perler et al., 1994, Nucleic Acids Res., 22, 1125-1127; Perler, F. B., 1998, *Cell*, 92, 1-4). All information and catalytic groups necessary to perform a self-splicing reaction reside in the intein and two flanking amino acids. The chemical mechanism of protein splicing is described in detail by Perler and colleagues (1997, *Curr. Opin. Chem. Biol.*, 1, 292-299) and by Shao & Kent (1997, *Chem. Biol.*, 4, 187-194). Inteins usually consist of N- and C-terminal splicing regions and a central homing endonuclease region or small linker region. Over 100 inteins are known so far that are distributed among the nuclear and organellar genomes of different organisms including eukaryotes, archaebacteria and eubacteria Perler, F. B., 2002, InBase, the Intein Database, *Nucleic Acids Res.* 30, 383-384). It was shown that inteins are capable of trans-splicing. The removal of the central homing endonuclease region does not have any effect on intein self-splicing. This made possible the design of trans-splicing systems, in which the N-terminal and C-terminal fragments of an intein are co-expressed as separate fragments and, when fused to exteins (protein fragments that are ligated together with the help of the Intein), can perform trans-splicing in vivo (Shingledecker et al., 1998, *Gene*, 207, 187-195). It was also demonstrated with N- and C-terminal segments of the *Mycobacterium tuberculosis* RecA intein, that protein trans-splicing can take place in vitro (Mills et al., 1998, *Proc. Natl. Acad. Sci. USA*, 95, 3543-3548). This phenomenon was also identified for DnaE protein of *Synechocystis* sp. strain PCC6803 (Wu et al, 1998, *Proc. Natl. Acad. Sci. USA*, 95, 9226-9231). Two different genes located more than 700 Kb.p. apart on opposite DNA strands encode this protein. It was also shown that two intein sequences encoded by those genes reconstitute a split mini-intein and are able to mediate protein trans-splicing activity when tested in *Esherichia coli* cells. An intein of the same origin (DnaE intein from *Synechocystis* sp. strain PCC6803) was used to produce functional herbicide-resistant acetolactate synthase II from two unlinked fragments (Sun et al., 2001, *Appl. Environ. Microbiol.*, 67, 1025-29) and 5-enolpyruvylshikimate-3-phosphate synthase (EPSPS) (Chen et al., 2001, *Gene*, 263, 39-48) in *E. coli*.

Trans-splicing of protein parts is not necessarily required to restore the original protein function. In many cases, affinity interaction between protein parts without peptide bond formation is sufficient to restore protein function. This approach is the most successful (as in the case of intein-mediated trans-splicing) with proteins having two or more functional domains. In such a case, the domains can be separated from each other by splitting the coding sequence between two transcription vectors and brought together through protein-mediated affinity interactions. Protein domains can interact without the necessity to use interacting intein parts. There is an example of reconstituting activity of IS10 transposase consisting of two structural domains connected by a proteolysis-sensitive linker region (Kwon, Chalmers & Kleckner, 1995, *Proc. Natl. Acad. Sci. USA*, 92, 8234-8238). Each of the domains separately is unable to provide for the transposase function. When added together, however, they are able to provide for transpositions even without being connected by a linker region. There are many other examples of functional protein reconstitution from isolated fragments without any peptide bond formation. The efficient assembly of a functional insulin receptor binding site was achieved by simple mixing of non-functional fragments (Kristensen et al., 2002, *J. Biol. Chem.*, 277, 18340-18345). Reconstitution of active proteins by simple mixing of two inactive peptide fragments was shown for leucine dehydrogenase (Oikawa et al., 2001, *Biochem. Biophys. Res. Commun.*, 280, 1177-1182), $Ca^{2+}$-binding protein calbindin D28k (Berggard et at, 2000, *Protein Sci.*, 9, 2094-2108; Berggard et al., 2001, *Biochemisty*, 40, 1257-1264), *Arabidopsis* developmental regulator COP1 (Stacey et al, 2000, *Plant Physiol.*, 124, 979-990), diopamine D receptor (Scarselli et al, 2000, *Eur. J. Pharmacol.*, 397, 291-296), microplasminogen (De Los Santos, Wang & Reich, 1997, *Ciba Found. Symp.*, 212, 76-83) and many others. Leucine zipper domains are of special interest for forming protein heterodimers once fused to a protein of interest (Riecker &

Hu, 2000, *Methods Enzymol.,* 328, 282-296; Liu et al., 2001, *Curr. Protein Pept. Sci.,* 2, 107-121). An interesting example is the control of protein-protein interaction with a small molecule. For example, Cre recombinase was engineered in such a way that, when split in two inactive fragments, was able to restore 100% of its recombinase activity in the presence of the small molecule rapamycin that triggered activity complementation by heterodimerization between two inactive fragments (Jullien et al., 2003, *Nucleic Acids Res.,* 31, e131). Rapamycin and its non-toxic homologues also can be used in conditional protein splicing, where they trigger trans-splicing reaction (Mootz et al., 2003, *J. Am. Chem. Soc.,* 125, 10561-10569). Similar approaches for regulation of protein-protein interactions with the help of small molecules, such as rapamycin or rapamycin analogues, are described e.g. by Amara et al., 1997, *Proc. Natl. Acad. Sci. USA.,* 94, 10618-10623; Pollock et al., 2000, *Proc. Natl. Acad. Sci. USA.,* 97, 13221-13226; Pollock et al., 2002, *Nat Biotechnol.,* 20, 729-733. Many other chemical dimerizers such as dexamethasone and methotrexate can be used for assembling active homo- or heterodimers from inactive protein fragments (for a review see: Pollock & Clackson, 2002, *Curr. Opin. Biotechnol.,* 13, 459-467).

Affinity interactions can be efficiently engineered by using naturally occurring interacting protein domains or by identifying such domains with the help of two-hybrid (Fields & Son, 1989, *Nature,* 340, 245-246; Chien et al., 1991, *Proc. Natl. Acad. Sci. USA,* 88, 9578-9582; *Yeast Protocol Handbook,* Clontech Laboratories, Inc., 2000) or phage display systems. For example, phage display may be used to select a 5-12-mer oligopeptide with high affinity to a protein fragment of interest. Several such systems are now commercially available. Phage display is a selection technique in which a short variable 5-12-mer oligopeptide is inserted into a coat protein of bacteriophage. The sequence encoding this variable oligopeptide is included in the corresponding gene of the bacteriophage coat protein. Usually, a 7-mer phage display library has at least $10^9$ independent clones bearing different combinations of 7-mer amino acids in variable oligopeptides. Phage display has been used to create affinity complexes between bacteriophage and a protein of interest, allowing rapid identification of peptide ligands for a given target protein by an in vitro selection process called "panning" (Parmley, Smith, 1988, *Gene* 73, 305-318; Cortese et al., 1995, *Curr. Opin. Biotechnol.,* 6, 73-80). The phage-protein complex created after panning procedure can be dissociated and a phage with affinity to a target protein can be amplified. Usually, one needs three panning cycles to get bacteriophage with high affinity. After three rounds, individual clones can be characterized by sequencing of variable region in genomic DNA. Said system can be efficiently adopted for identifying short interacting oligopeptides and using them as affinity tags in order to bring together protein fragments.

Another approach includes the use of naturally occurring interacting domains like leucine-rich repeats (Kobe & Deisenhofer, 1994, *Trends Biochem Sci.,* 19, 415-421; Kobe & Kajava, 2001, *Curr. Opin. Struct. Biol.,* 11, 725-732), zinc finger (Grossley, Merika & Orkin, 1995, *Mol. Cell. Biol.,* 15, 2448-2456), ankyrin repeats (Thompson, Brown & McKnight, 1991, *Science,* 253, 762-768), chromo domains (Paro & Hogness, 1991, *Proc. Natl. Acad. Sci. USA,* 88, 263-267; Singh et al., 1991, *Nucleic Acids Res.,* 19, 789-793) and many others involved in protein-protein interactions. However, the possibility of involving in protein-protein interactions not only the engineered protein fragments containing the motive fusions, but also endogenous proteins may be taken into account.

Spread of the Protein Switch within a Plant Host for Triggering a Cellular Process of Interest Herein, an approach for overcoming the restrictions of the low number of cells of a plant that can be reached by the externally-applied signal, notably by said polypeptide, is provided: said signal may lead to the formation of an intracellular protein-switch molecule capable of cell-to-cell or systemic movement. Moreover, said signal may lead to the formation of a virus-based vector (amplicon) expressing a gene of interest or a part thereof and being capable of cell-to cell or systemic movement in said plant. In these approaches, the movement of either viral vectors or protein-switch molecules or both can lead to the spread of a cellular process and/or biochemical cascade over significant parts of said plant and even all over the genetically-modified plant.

In example 1, an externally delivered recombinase triggers the expression of an intracellular recombinase capable of cell-to-cell movement due to its fusion with a viral movement protein (MP) and switching on the expression of itself in the cells it reaches (see FIG. 3). The recombinase is also capable of triggering the expression of a gene of interest (GUS gene) in the cells it reaches.

In Example 2, the protein switch contains a recombinase to convert a precursor vector of a viral vector into the viral vector. The viral vector is capable of amplification, cell-to-cell and systemic movement. Integrase-mediated recombination at loxP sites of pICHGFPinv (FIG. 4-A) leads to the inversion of a DNA fragment flanked by said sites and formation of a viral vector capable of amplification and expression of a gene of interest (GFP) (FIG. 4-B). This is achieved as the result of placing viral components (3'NTR—3'non-translated region; CP—coat protein) necessary for vector amplification and systemic transport in sense orientation relative to a promoter active in the multi-cellular organism in question like the actin 2 promoter. Thus, together with other viral vector components (RdRp and CP) it forms a cDNA which upon actin 2 promoter-driven transcription forms an RNA viral vector capable of amplification, cell-to-cell and systemic movement. Optionally, said vector can be further modified by removing the CP (coat protein) gene. Such a vector lacking the CP gene will still be capable of cell-to-cell movement. The construction of plant virus-based expression systems for the expression of non-viral genes in plants has been described in several papers (Dawson et al., 1989, *Virology,* 172, 285-293; Brisson et al., 1986, *Methods in Enzymology,* 118, 659; MacFarlane & Popovich, 2000, *Virology,* 267, 29-35; Gopinath et al., 2000, *Virology,* 267, 159-173; Voinnet et al., 1999, *Proc. Natl. Acad. Sci. USA,* 96, 14147-14152) and reviews (Porta & Lomonossoff, 1996, *Mol. Biotechnol.,* 5, 209-221; Yusibov et al., 1999, *Curr. Top. Microbiol. Immunol,* 240, 81-94) and can be easily performed by those skilled in the art. Viral vector-based expression systems offer a significantly higher yield of a transgene product compared to plant nuclear transgenes. For example, the level of transgenically encoded protein can reach 5-10% of the total cellular plant protein content when expressed from a viral vector (Kumagai et al., 2000, *Gene,* 245, 169-174; Shivprasad et al., 1999, *Virology,* 255, 312-323). RNA viruses are the most suitable as they offer a higher expression level compared to DNA viruses. There are several published patents which describe viral vectors suitable for systemic expression of transgenic material in plants (U.S. Pat. No. 5,316,931; U.S. Pat. No. 5,589,367; U.S. Pat. No. 5,866,785). In general, these vectors can express a foreign gene as a translational fusion with a viral protein (U.S. Pat. No. 5,491,076; U.S. Pat. No. 5,977,438), from an additional subgenomic promoter (U.S. Pat. No. 5,466,788; U.S. Pat. No. 5,670,353; U.S. Pat.

No. 5,866,785), or from polycistronic viral RNA using IRES (internal ribosome entry site) elements for independent protein translation (German Patent Application DE 10049587). The first approach—translational fusion of a recombinant protein with a viral structural protein (Hamamoto et al., 1993, BioTechnology, 11, 930-932; Gopinath et al., 2000, Virology, 267, 159-173; JP6169789; U.S. Pat. No. 5,977,438) gives significant yield of a recombinant protein product. However, the usefulness of this approach is limited, as the recombinant protein cannot be easily separated from the viral one. An alternative of this approach employs a translational fusion via a peptide sequence recognized by a viral site-specific protease or via a catalytic peptide (Doija et al., 1992, Proc. Natl. Acad. Sci USA, 89, 10208-10212; Gopinath et al., 2000, Virology, 267, 159-173; U.S. Pat. No. 5,162,601; U.S. Pat. No. 5,766,885; U.S. Pat. No. 5,491,076). Expression processes utilizing viral vectors built on heterologous subgenomic promoters provide the highest level of protein production to date (U.S. Pat. No. 5,316,931). The most serious disadvantage of viral vectors and many others is their limited capacity with regard to the size of DNA to be amplified. Usually, stable constructs accommodate inserts of not more than one kb. In some areas of plant functional genomics this may not be such a serious limitation, as G. della-Cioppa et al. (WO993651) described the use of TMV-based viral vectors to express plant cDNA libraries with the purpose of silencing endogenous genes. Two-component amplification systems which make use of helper viruses may offer a slightly better capacity (U.S. Pat. No. 5,889,191). Other systems based on expression cassettes that are stably integrated into the plant genome contain the strong 35S promoter driving the expression of viral vector based amplicons. These systems usually are subject to post-transcriptional gene silencing (PTGS) (Angell & Baulcombe, 1997, EMBO J., 16, 3675-3684). The use of PTGS suppressors is necessary to overcome such silencing (WO0138512). It requires to perform crosses between plants carrying the silenced amplicon and plants carrying the source of PTGS suppressor (Mallory et al., 2002, Nature Biotechnol., 20, 622-625) for achieving large scale production of a protein of interest with the help of such system. Evidently, such a system has no flexibility and no tight control over transgene expression and is restricted to the production of proteins which do not compromise plant growth and development.

Our approach allows to overcome the limitations of the above-described viral vector systems, specifically their limited capacity for the size of the gene to be expressed and the lack of flexibility in controlling the expression. In our invention, the viral vector precursor (or provector) is preferably present in each cell of the transgenic plant. In the case of expression of large genes (above 1 Kb), protein-switch movement is preferred over viral vector movement. Viral vectors can efficiently amplify in cells and the size of the insert of a viral vector mostly affects the ability for cell-to-cell and systemic movement. Therefore, providing a moveable protein-switch capable of activating a viral vector to many cells or even to all cells of the host plant will solve the above-mentioned problem. Additionally, to provide a system with an efficient switching function that is able to turn on the amplification of such a viral vector in most if not all cells of the host plant, protein-switches capable of cell-to-cell/systemic movement are used in the present invention.

To this end, the protein-switch may contain a protein portion that renders said protein capable of cell-to-cell and/or systemic movement Examples of such protein portions capable to intercellular trafficking are known in prior art. There is evidence that plant transcription factors, defense-related proteins and viral proteins can traffic through plasmodesmata (for review see: Jackson & Hake, 1997, Curr. Opin. Genet Dev., 7, 495-500; Ding, B. 1998, Plant Mol. Biol., 38, 279-310; Jorgensen R A., 2000, Sci STKE, 58, PE2; Golz & Hudson, 2002, Plant Cell, 14 S277-S288). It was shown that a fusion of 3a movement protein of Cucumber mosaic virus with GFP can traffic out via plasmodesmata to neighboring cells (Itaya et al., 2002, Plant Cell, 14, 2071-2083). Such fusion also showed the movement through phloem from transgenic rootstock into non-transgenic scion. The movement protein of tobacco mosaic virus (TMV), P30, traffics between cells through plasmodesmata and, by affecting plasmodesmata size, facilitates the movement of many other large macromolecules not specified for such movement (Citovsky et al., 1999, Phil. Trans. R Soc. London B Biol Sci., 354, 637-643; Ding, Itaya & Woo, 1999, Int Rev. Cytol., 190, 251-316). The P30:GFP fusion showed movement between the cells independent of physiological conditions, while the non-targeted GFP diffusion through plasmodesmata at large depends of physiological state of the plant cells (Crawford & Zambryski, 2001, Plant Physiol., 125, 1802-1812). The fusion of GFP with transcription factor knotted1 also showed the ability for intercellular trafficking. The GFP:KN1 fusion protein demonstrated movement from internal tissues of the leaf to the epidermis, between epidermal cells and into the shoot apical meristem of tobacco plant (Kim et al., 2002, Proc. Natl. Acad. Sci. USA, 99, 4103-4108). Plasmodesmata play an important role in such trafficking and its physiological stage and structure are important for the efficiency of such trafficking. For example, simple plasmodesmata allow the nonspecific trafficking of proteins in developing tobacco leaves, while the branched ones do not (Oparka et al., 1999, Cell, 98, 5-8). Allowing trafficking of macromolecules including proteins appears to be a normal function of plasmodesmata, which was made use of by plant viruses for their cell-to-cell spread (Fujiwara et al., 1993, Plant Cell, 5, 1783-1794). In general, it is evident that plasmodesmata and the phloem play an important role in the transport and delivery of information macromolecules (proteins and nucleic acids) (Ruiz-Medrano et al., 2001, Curr. Opin. Plant Biol., 4, 202-209). Phloem sap proteins from *Cucurbita maxima* and *Ricinum communis* have the capacity of cell-to-cell trafficking through plasmodesmata (Balachandran et al., 1997, Proc. Natl. Acad. Sci. USA., 94, 14150-14155). There are also abundant data about engineering intercellular trafficking of protein of interest in mammalian cells, predominantly for therapeutical purposes, by fusing said protein with polypeptide of viral origin having the transport function (U.S. Pat. No. 6,358, 739; U.S. Pat. No. 6,184,038; U.S. Pat. No. 6,316,252). For example, the herpes simplex virus type 1 (HSV-1) virion protein VP 22 exhibits remarkable properties of intercellular trafficking even when it is fused to another protein. Said virion protein is used for therapeutic purposes, as the fusion with the entire p53 protein (Phelan et al., 1998, Nat. Biotechnol., 16, 440-443; Zendel et al., 2002, Cancer Gene Ther., 9, 489-496), with glucocorticoid receptor (Soden et al., 2002, J. Endocrinol, 172, 615-625). Another HSV protein, US11, also has intercellular trafficking activity. This was demonstrated by fusing said protein to green fluorescent protein GFP (Koshizuka et al., 2001, Biochem. Biophys. Res. Commun., 288, 597-602). The TAT protein of human immunodeficiency virus (HIV) in parallel with VP22 protein was used for intercellular delivery of a polypeptide having cell immortalization activity (U.S. Pat. No. 6,358,739).

FIG. 5 shows schematically possibilities of achieving intercellular movement of the protein switch of the invention. An externally-applied signal (e.g. said polypeptide) and the protein switch synthesized within a cell can be fusions of the same or different protein segments to translocating or trafficking signals. In our example (FIG. 4), the same protein segment, e.g. a recombinase is fused either with a membrane translocating signal (MTS) for cell membrane permeability, thus serving as external signal, or with a protein portion (TP) providing for intercellular trafficking. It is very likely that for small proteins (like GFP and smaller), fusion to TP might not be necessary, as they may be capable of highly efficient cell-to-cell movement through simple diffusion. However, for larger protein switches, fusion with a TP or an active fragment thereof is advantageous. It is evident that among all proteins involved in intercellular trafficking, viral proteins are studied the best. They are the most preferred candidates to be included in a protein switch. As is shown in FIG. 5, an externally delivered polypeptide (MTS:recombinase) may trigger the expression of a transgene encoding a protein switch having the same enzymatic activity (recombinase:TP), but that is capable of leaving a cell and entering other cells (intercellular trafficking). Said protein switch capable of trafficking triggers protein switch expression in all affected cells, what represents a chain reaction. Availability of said protein switch in the cell is a prerequisite for triggering the expression of a gene of interest (GOI) in cells by DNA rearrangement, causing viral vector-based amlicon formation. The size of the gene of interest expressed from such an amplicon is not a limiting factor for efficient GOI expression, since amplicon stability and cell-to-cell movement are not necessary in this system: the viral provector may be present in each plant cell and the spreading of the protein switch may trigger the expression of the gene of interest in each of these cells. Preferably, however, spreading of the amplicon contributes to efficient GOI expression.

In example 3 of this invention we describe an approach of addressing the issue of the size of a protein that is chosen for the function of the protein-switch. For example, the integrase phiC31 (encoded by almost 2 kb cDNA might be too large for an efficient intercellular trafficking after fusion to a protein responsible for cell-to-cell movement. In such case we use the split protein approach, where only a part of the intracellular protein switch is capable of intercellular trafficking, while the other part is expressed without any restriction by the eucaryotic cells (FIG. 6). In this specific example, the functional protein switch is assembled through intein-mediated protein trans-splicing. However, simple affinity interactions between the split protein parts can also restore its functionality.

The ultimate purpose of the protein switch system contemplated herein is an operational control of a cellular process of interest or a cascade of biochemical reactions of interest in a plant production system. A biochemical cascade is a chain of biochemical reactions in a host production system that ultimately yields a specific product, effect, or trait of interest.

Preferred plants for the use in this invention include any plant species with preference given to agronomically and horticulturally important species. Common crop plants for the use in present invention include alfalfa, barley, beans, canola, cowpeas, cotton, corn, clover, lotus, lentils, lupine, millet, oats, peas, peanuts, rice, rye, sweet clover, sunflower, sweetpea, soybean, sorghum triticale, yam beans, velvet beans, vetch, wheat, wisteria, and nut plants. The plant species preferred for practicing this invention include representatives of Gramineae, Compositeae, Solanaceae and Rosaceae. Solanaceae are preferred.

Additionally, preferred species for use the invention, as well as those specified above, plants from the genera: *Arabidopsis, Agrostis, Allium, Antirrhinum, Apium, Arachis, Asparagus, Atropa, Avena, Bambusa, Brassica, Bromus, Browaalia, Camellia, Cannabis, Capsicum, Cicer, Chenopodium, Chichorium, Citrus, Coffea, Coix, Cucumis, Curcubita, Cynodon, Dactylis, Datura, Daucus, Digitalis, Dioscorea, Elaeis, Eleusine, Festuca, Fragada, Geranium, Glycine, Helianthus, Heterocallis, Hevea, Hordeum, Hyoscyamus, Ipomoea, Lactuca, Lens, Lilium, Linum, Lolium, Lotus, Lycopersicon, Majorana, Malus, Mangifera, Manihot, Medicago, Nemesia, Nicotiana, Onobrychis, Oryza, Panicum, Pelargonium, Pennisetum, Petunia, Pisum, Phaseolus, Phleum, Poa, Prunus, Ranunculus, Raphanus, Ribes, Ricinus, Rubus, Saccharum, Salpiglossis, Secale, Senecio, Setaria, Sinapis, Solanum, Sorghum, Stenotaphrum, Theobroma, Trifolium, Trigonella, Triticum, Vicia, Vigna, Vitis, Zea*, and the Olyreae, the Pharoideae and many others.

Within the scope of this invention the plant species which are not included into the food or feed chain are specifically preferred for pharmaceutical and technical protein production. Among them, *Nicotiana* species are the most preferred, as a species easy to transform and to cultivate with well developed expression vectors (especially viral vectors) systems.

Preferred multicellular systems of non-plant origin to be used within the scope of this invention would be the cell cultures of mammalian origin, insect cell cultures, non-human transgenic organisms.

Genes of interest, their fragments (functional or non-functional) and their artificial derivatives that can be expressed and isolated using our invention include, but are not limited to: starch modifying enzymes (starch synthase, starch phosphorylation enzyme, debranching enzyme, starch branching enzyme, starch branching enzyme II, granule bound starch synthase), sucrose phosphate synthase, sucrose phosphorylase, polygalacturonase, polyfructan sucrase, ADP glucose pyrophosphorylase, cyclodextrin glycosyltransferase, fructosyl transferase, glycogen synthase, pectin esterase, aprotinin, avidin, bacterial levansucrase, *E. coli* glgA protein, MAPK4 and orthologues, nitrogen assimilation/metabolism enzyme, glutamine synthase, plant osmotin, 2S albumin, thaumatin, site-specific recombinase/ntegrase (FLP, Cre, R recombinase, Int, SSVI Integrase R, Integrase phiC31, or an active fragment or variant thereof), isopentenyl transferase, Sca M5 (soybean calmodulin), coleopteran type toxin or an insecticidally active fragment, ubiquitin conjugating enzyme (E2) fusion proteins, enzymes that metabolise lipids, amino acids, sugars, nucleic acids and polysaccharides, superoxide dismutase, inactive proenzyme form of a protease, plant protein toxins, traits altering fiber in fiber producing plants, Coleopteran active toxin from *Bacillus thuringiensis* (Bt2 toxin, insecticidal crystal protein (ICP), CryIC toxin, delta endotoxin, polyopeptide toxin, protoxin etc.), insect specific toxin AaIT, cellulose degrading enzymes, E1 cellulase from *Acidothermus celluloticus*, lignin modifying enzymes, cinnamoyl alcohol dehydrogenase, trehalose-6-phosphate synthase, enzymes of cytokinin metabolic pathway, HMG-CoA reductase, thaumatin, *E. coli* inorganic pyrophosphatase, seed storage protein, *Erwinia herbicola* lycopen synthase, ACC oxidase, pTOM36 encoded protein, phytase, ketohydrolase, acetoacetyl CoA reductase, PHB (polyhydroxybutanoate) synthase, acyl carrier protein, napin, EA9, non-higher plant phytoene synthase, pTOM5 encoded protein, ETR (ethylene receptor), plastidic pyruvate phosphate dikinase, nematode-inducible transmembrane pore protein, trait enhancing photosynthetic or plastid function of the plant cell, stilbene synthase, an enzyme capable of hydroxylating phenols, catechol dioxygenase, catechol 2,3-dioxygenase, chloromuconate cycloisomerase, anthranilate synthase, *Brassica* AGL15 protein, fructose 1,6-biphosphatase (FBPase), AMV RNA3, PVY replicase, PLRV replicase, potyvirus coat protein, CMV coat protein, TMV coat protein, luteovirus replicase, MDMV messenger RNA, mutant geminiviral replicase, *Umbellularia californica* C12:0 preferring acyl-ACP thioesterase, plant C10 or C12:0 preferring acyl-ACP thioesterase, C14:0 preferring acyl-ACP thioesterase (luxD), plant synthase factor A, plant synthase factor B, D6-desaturase, protein having an enzymatic activity in the peroxysomal b-oxidation of fatty acids in plant cells, acyl-CoA oxidase, 3-ketoacyl-CoA thiolase, lipase, maize acetyl-CoA-carboxylase, 5-enolpyruvylshikimate-3-phosphate synthase (EPSP), phosphinothricin acetyl transferase (BAR, PAT), CP4 protein, ACC deaminase, protein having posttranslational cleavage site, DHPS gene conferring sulfonamide resistance, bacterial nitrilase, 2,4-D monooxygenase, acetolactate synthase or acetohydroxyacid synthase (ALS, AHAS), polygalacturonase, Taq polymerase, bacterial nitrilase, many other enzymes of bacterial or phage including restriction endonucleases, methylases, DNA and RNA ligases, DNA and RNA polymerases, reverse trascryptases, nucleases (Dnases and RNAses), phosphatases, transferases etc.

This invention also can be used for the purpose of molecular farming and purification of commercially valuable and pharmaceutically important proteins including industrial enzymes (cellulases, lipases, proteases, phytases etc.) and fibrous proteins (collagen, spider silk protein, etc.). Any human or animal health protein can be expressed and purified using described in our invention approach. Examples of such proteins of interest include inter alia immune response proteins (monoclonal antibodies, single chain antibodies, T cell receptors etc.), antigens including those derived from pathogenic microorganisms, colony stimulating factors, relaxins, polypeptide hormones including somatotropin (HGH) and proinsulin, cytokines and their receptors, interferons, growth factors and coagulation factors, enzymatically active lysosomal enzyme, fibrinolytic polypeptides, blood clotting factors, trypsinogen, a1-antitrypsin (AAT), human serum albumin, glucocerebrosidases, native cholera toxin B as well as function-conservative proteins like fusions, mutant versions and synthetic derivatives of the above proteins.

Further embodiments and examples that may be combined with the present invention can be found in DE 102 54 167 and in DE 102 54 166.

EXAMPLE 1

Detection of the Amplification and Movement of a Protein Switch Using a Gus Test Construct Stably Integrated into the Plant Genome Construct pICHrecomb (FIG. 3) contains the cre recombinase fused to the TMV movement protein (MP) followed by a transcription terminator. The fusion protein cannot be expressed as it is not under control of a promoter, and is located between two loxP sites in opposite orientation. This cassette (Recombinase-MP fusion-terminator between Lox sites) is inserted in antisense orientation downstream of the *Arabidopsis* actin2 promoter. Flipping of the recombinase cassette by action of Cre recombinase (provided externally as said polypeptide of the invention) will place the recombinase-MP gene under control of the Actin 2 promoter and result in its expression.

PICHtestGus is a test construct designed to detect expression of cre recombinase. It contains, on a binary vector, the 35S promoter followed by a LoxP site, the GFP ORF, the Nos terminator, a second Lox P site in direct orientation, the Gus ORF and the Ocs terminator. As such, the Gus gene is not expressed as it is not directly fused to a promoter. Expression of cre recombinase leads to excision of GFP and the Nos terminator, placing the Gus gene under control of the 35S promoter.

Transgenic *Nicotiana benthamiana* plants containing the T-DNA of pICHtestGus or pICHrecomb were obtained by *Agrobacterium*-mediated transformation of leaf discs as described by Horsch et al., (1985, Science, 227, 129-131). Leaf discs were incubated for 30 min with *Agrobacterium* strain GV3101 transformed with either construct. After three days of incubation on medium (MS-medium 0.1 mg/l NAA, 1 mg/l BAP) without selective agent, selection of transformants was performed on the same MS-medium supplemented with 100 mg/L Kanamycin. In order to reduce the growth of *Agrobacterium*, the medium was also supplemented with 300 mg/L carbenicilin and 300 mg/L cefotaxime. Regenerants were incubated on selective MS-medium without hormones supplemented with the same concentration of the selective agents to induce rooting. The presence of the transgene in segregating T2-populations was confirmed by PCR-analysis. Plants containing both constructs (pICHtestGus and pICHrecomb) were obtained by hybridization of individual transformants. Identification of plants containing both constructs was performed using PCR.

Excised leaves of *Nicotiana benthamiana* plants containing both constructs were bombarded with construct pICH3981 (cre under control of the *Arabidopsis* actin2 promoter). As a control, *Nicotiana benthamiana* plants containing only the T-DNA of construct pICHtestGus were also bombarded with pICH3981. Bombarded leaves were kept in petri dishes with a piece of wet filter paper to keep the leaves alive for several days. After 5 days, the leaves were stained with an X-gluc solution. Bombarded leaves of transformants containing the T-DNA of constructs pICHtestGus alone exhibited many individually stained cells, which is what is expected from cells receiving cre by bombardment. In contrast, bombarded leaves of transformants containing the T-DNAs of both contructs pICHtestGus and pICHrecomb exhibited many patches of blue stained cells, indicating that activation of the recombinase-MP gene fusion lead to the movement to neighbouring cells where it could activate its own expression as well as recombine the test construct.

EXAMPLE 2

Use of a Protein Switch Containing a Site-Specific DNA Recombinase Capable of Intercellular Trafficking for Assembling an Amplicon from Provector Parts that are Stably Integrated into the Plant Genome: GFP Expression A binary vector pICHFPinv (FIG. 4) carrying T-DNA with two provector parts was made using standard molecular biology techniques (Maniatis et al., 1982, Molecular cloning: a Laboratory Manual. Cold Spring Harbor Laboratory, New York). Descriptions of provector elements and basic principles of their construction and function are described in detail in patent application WO02/88369 (PCT/EP02/03476) and in DE 101 21 283. The vector contains a transformation marker (NPTII gene) and the 5' end of TMV (including the RNA dependent RNA polymerase [RdRp], the movement protein [MP] followed by a subgenomic promoter) preceded by the *Arabidopsis* actin 2 promoter (An et al., 1996, *Plant J.*, 10, 107-121). The vector also contains the 3' end of the provector which contains the gene of interest (GFP), the viral coat protein (CP, providing for systemic movement), the 3'-nontranslated region of the viral vector (3' NTR) and a transcription terminator. The 3' provector part is flanked by LoxP sites in opposite orientation and is positioned on the vector in opposite orientation relative to the 5' provector.

Therefore, this construct as such cannot lead to TMV vector amplification. Application of cre recombinase leads to flipping of the 3' provector part and to formation of a functional vector (FIG. 4B, FIG. 5). The TMV-based RNA amplicon expressing GFP is capable of cell-to-cell and systemic movement. GFP expression in *N. benthamiana* plants can be easily detected visually by using a UV lamp or by observing plant tissue under a LEICA stereo fluorescent microscope system (excitation at 450-490 nm, emission at 500-550 nm). The sGFP used in our experiments can be excited by blue and UV-light (sGFP stands for a synthetic GFP).

Transgenic *Nicotiana benthamiana* plants containing the T-DNA of pICHGFPinv were obtained by *Agrobacterium*-mediated transformation of leaf discs as described above.

Figure 7A:
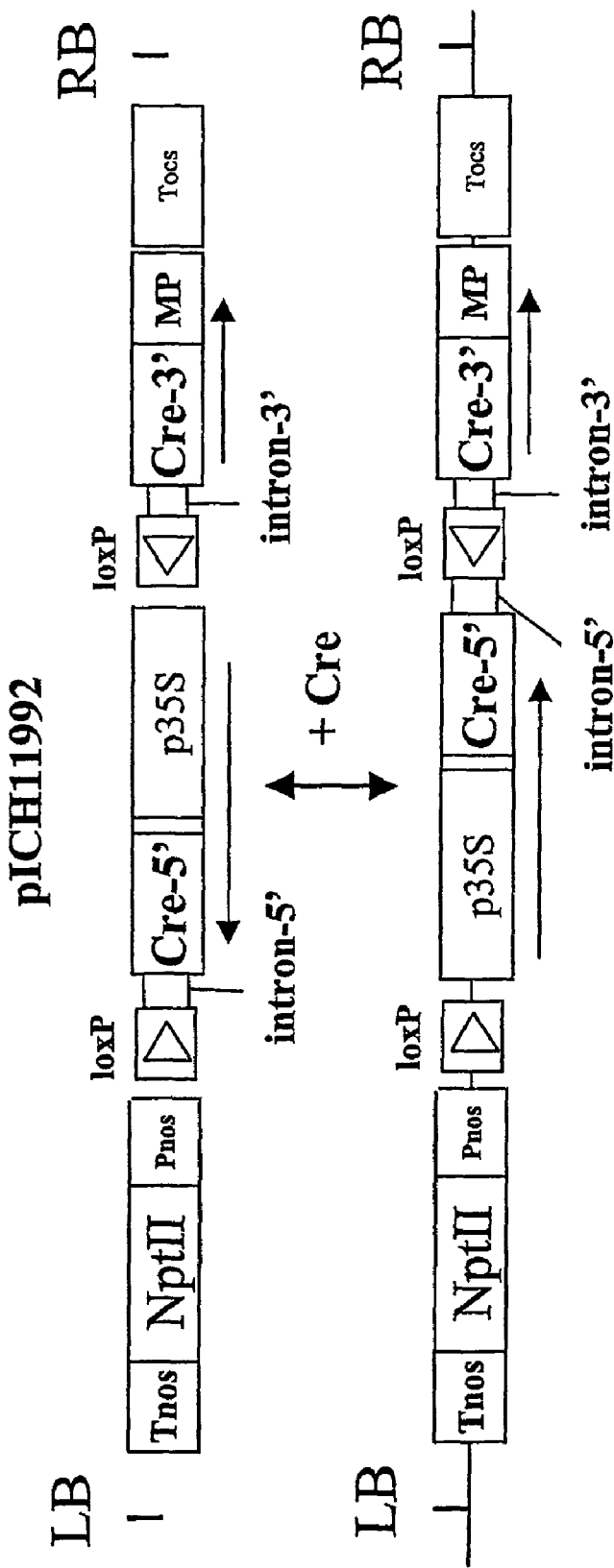
Figure 7B:
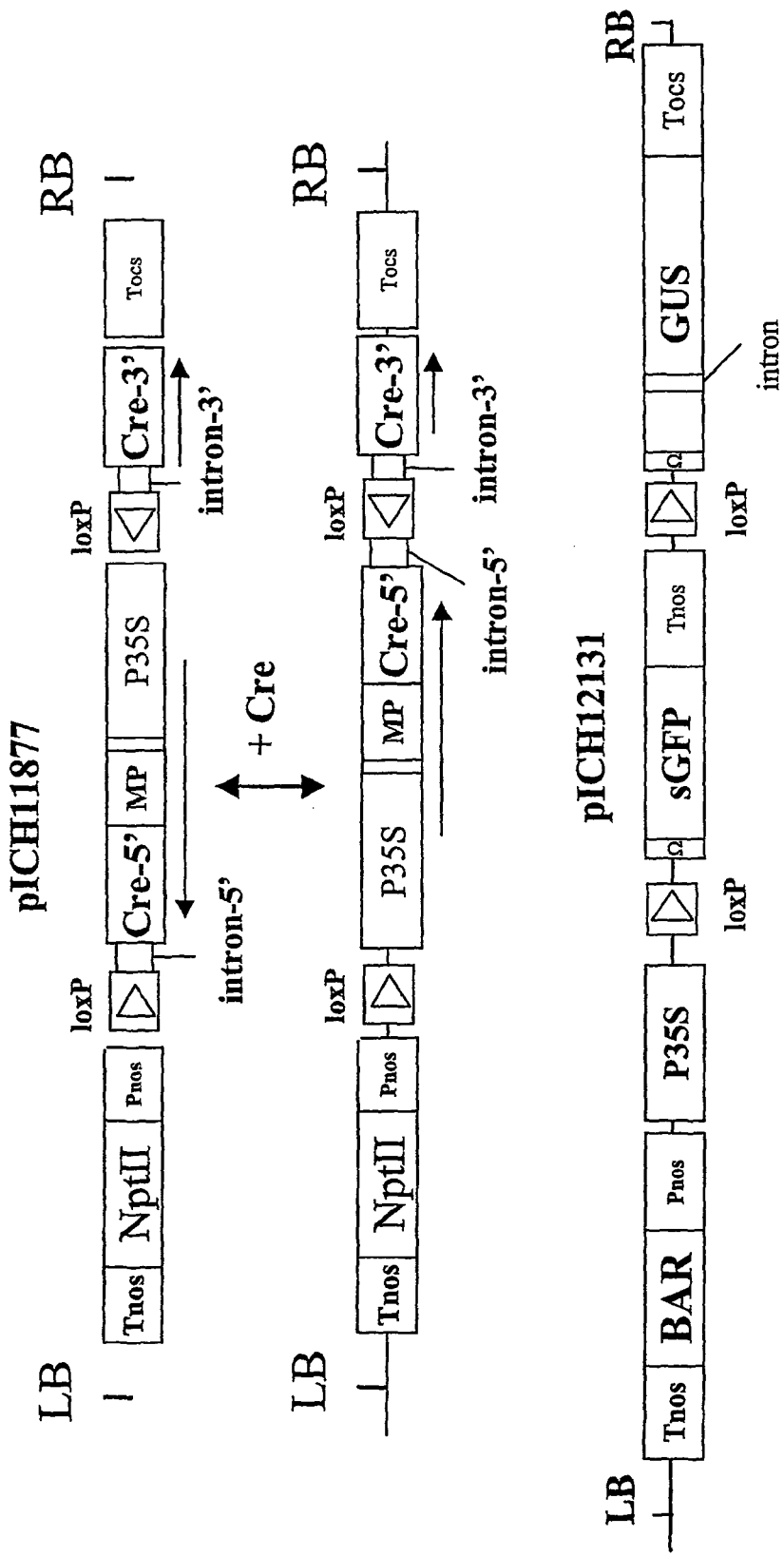

Other examples of using a protein switch capable of cell-to cell movement are shown in FIG. 7. The constructs pICH11992 (FIG. 7A) and pICH11877 are designed for switching Cre recombinase capable of cell-to-cell movement from heterologous DNA stably incorporated into a plant nuclear chromosome. The cre recombinase gene is activated upon flipping of a part of the construct encoding the N-terminal end of the cre protein. This approach allows triggering the process of functional recombinase synthesis by externally delivered cre recombinase. The progeny of transgenic plants with T-DNA of pICH11877 or pICH11992 crossed with *Nicotiana benthamiana* plant carrying T-DNA of pICH12131 (FIG. 7B) are able to express the GUS gene upon activation with an externally applied cre recombinase.

Delivery of Said Polypeptide by Agro-Infiltration

Agroinfiltration of transgenic tobacco plants was performed according to a modified protocol described by Yang et al., 2000, *Plant Journal*, 22(6), 543-551. *Agrobacterium tumefaciens* strain GV3101 transformed with individual constructs to provide for externally applied protein-switch, was grown in LB-medium supplemented with Rifampicin 50 mg/l and carbenicilin 50 mg/l. *Agrobacterium* cells of an overnight culture (5 ml) were collected by centrifugation (10 min, 4500 g) and resuspended in 10 mM MES (pH 5.5) buffer supplemented with 10 mM $MgSO_4$. The bacterial suspension was adjusted to a final $OD_{600}$ of 0.8. In case of delivery of several constructs, agrobacterial clones carrying different constructs were mixed before infiltration.

Agroinfiltration was conducted on near fully expanded leaves that were still attached to the intact plant. The bacterial suspension was infiltrated with a 5 ml syringe. By infiltrating 100 µl of bacterial suspension into each spot (typically 3-4 $cm^2$ of infiltrated area) eight to 16 spots separated by veins could be placed in a single tobacco leaf. After infiltration, plants were further grown under greenhouse conditions at 22° C. and 16 h light per day.

Seven days after infiltration with *agrobacterium* carrying a binary vector with a T-DNA region encoding cre recombinase, infiltrated leaves of transgenic tobacco plants (pICHG-FPinv, *Nicotiana tabacum*) showed growing sectors of strong GFP-expression which could be observed under UV-light on intact plants. No GFP-expression was visible on leaves of non-transformed tobacco plants infiltrated with the same *agrobacterium*.

EXAMPLE 3

Use of a Split Protein Switch

In order to make a movable switch protein smaller in size, we have split the phage integrase phiC31 (Thomason, Calendar & Ow, 2001, *Mol. Genet. Genomics*, 265, 1031-1038), using the *synechocystis* sp. PCC6803 DnaE gene intein. The integrase was split into N and C terminal fragments (pICHRecC and pICHRecN), and the C terminal frament was fused to the MP gene (FIG. 6). The integrase fragment in pICHrecC it is flanked by recombination sites AttP and AttB, and is inactive as it is not under control of a promoter. Recombination between AttB and AttP sites will lead to recombination and flipping of the integrase fragment, placing it under control of the 35S promoter. The N fragment of the integrase in pICHRecN is expressed constitutively in plants, but functional integrase will be formed only after recombination of the pICHrecC T-DNA, expression of the C terminal integrase fragment and intein-mediated integrase assembly. To start the process, the integrase can be supplied exogenously.

To assay integrase expression and movement, a test construct, pICHtestGus2, was made. This construct is similar to construct pICHtestGus except that the LoxP sites have been replaced with recombination sites AttB and AttP.

All three constructs pICHtestGus2, pICHRecC and pICHrecN were transformed in *Agrobacterium* bacterium GV3101 and used for *Nicotiana benthamiana* transformation. In a similar assay as described in example 1, excised *N. benthamiana* leaves of plants transformed with all three constructs or transformed with the test construct alone were bombarded with pICP1010 (integrase under control of the *Arabidopsis* actin2 promoter). After staining with an X-gluc solution, patches of Gus-stained cells could be observed in leaves of transformants containing all three constructs, while only individual Gus-stained cells could be detected in leaves of transformants for the test construct alone.

The invention claimed is:

1. A method of controlling a genetically-modified multi-cellular plant organism or a part thereof, comprising the following steps:
   (a) providing a multi-cellular plant organism or a part thereof, whereby cells of said multi-cellular plant organism or said part contain a heterologous nucleic acid encoding a protein, wherein cells of said multi-cellular plant or part thereof contain an additional heterologous nucleic acid; and
   (b) causing expression of the protein from said heterologous nucleic acid in at least some of said cells by delivering a polypeptide to the multi-cellular plant organism or part thereof, said polypeptide rendering said heterologous nucleic acid expressible, said polypeptide having the activity of a site-specific recombinase rendering said heterologous nucleic acid expressible;
   wherein said protein
      (i) contains a protein portion enabling leaving a cell and entering other cells of said multi-cellular plant organism or a part thereof, wherein said protein portion is a domain of a viral movement protein, or a domain of a viral coat protein;
      (ii) causes expression of said protein from said heterologous nucleic acid in cells containing said heterologous nucleic acid by a DNA modifying activity of a segment of said protein, said segment having the activity of a site-specific recombinase, wherein the enzymatic activity of said protein is the same as the enzymatic activity of said polypeptide; and
      (iii) controls transcription of an RNA-viral amplicon from said additional heterologous nucleic acid contained in cells of said multi-cellular plant organism or a part thereof;
      wherein,
         a. the sequence encoding the RNA-viral amplicon is, in said additional heterologous nucleic acid, separated from a promoter by a sequence block that precludes an operable linkage between the sequence encoding the RNA-viral amplicon and the promoter; said sequence block being flanked by recombination sites such that said block can be cut out by a recombinase recognizing said recombination sites; or
         b. in said additional heterologous nucleic acid, a portion of a sequence necessary for transcription of the RNA-viral amplicon is in flipped orientation and flanked by recombination sites such that said sequence portion can flip back in correct orientation by a recombinase recognizing said recombination sites;
      thereby, operable linkage for transcription of the sequence encoding the RNA-viral amplicon can be established by the action of said protein.

2. The method of claim 1, wherein said polypeptide comprises a membrane translocation sequence for enabling entering of said polypeptide into a cell of said multi-cellular plant organism or of a part thereof.

3. The method of claim 1, wherein the delivery of said polypeptide does not involve introduction of nucleic acids in cells that code for said polypeptide or for a part of said polypeptide.

4. The method of claim 1, wherein said polypeptide is applied by a pathogenic microorganism that has a system of delivery of a polypeptide into a host cell.

5. The method of claim 4, wherein said pathogenic microorganism is a virulent or non-virulent *Agrobacterium*.

6. The method of claim 1, wherein said multi-cellular plant organism or part thereof provided in step (a) is a transgenic multi-cellular plant organism containing said heterologous nucleic acid stably integrated in the nuclear and/or the plastid genome of the cells.

7. The method of claim 1, wherein said additional heterologous nucleic acid is stably integrated in the genome of said multi-cellular plant organism or part thereof.

8. The method of claim 1, wherein said multi-cellular plant organism is a higher plant.

9. A genetically-modified multi-cellular plant organism or a part thereof containing a heterologous nucleic acid and an additional heterologous nucleic acid in cells thereof, whereby said heterologous nucleic acid is adapted such that
   (a) expression of a protein from said heterologous nucleic acid can be caused in cells containing said heterologous nucleic and
   (b) said protein contains a protein portion enabling said protein of leaving a cell and entering other cells of said multi-cellular plant organism or a part thereof, wherein said protein portion is a domain of a viral movement protein, or a domain of a viral coat protein, and
   (c) said protein has a segment having a modifying activity, said segment having the activity of a site-specific recombinase rendering said heterologous nucleic acid expressible, whereby said protein causes expression of said protein from said heterologous nucleic acid in cells containing said heterologous nucleic acid, and
   (d) said protein controls transcription of an RNA-viral amplicon from said additional heterologous nucleic acid contained in cells of said multi-cellular plant organism or a part thereof;
      wherein,
         (i) the sequence encoding the RNA-viral amplicon is, in said additional heterologous nucleic acid, separated from a promoter by a sequence block that precludes an operable linkage between the sequence encoding the RNA-viral amplicon and the promoter; said sequence block being flanked by recombination sites such that said block can be cut out by a recombinase recognizing said recombination sites; or
         (ii) in said additional heterologous nucleic acid, a portion of a sequence necessary for transcription of the RNA-viral amplicon is in flipped orientation and flanked by recombination sites such that said sequence portion can flip back in correct orientation by a recombinase recognizing said recombination sites;
      thereby, operable linkage for transcription of the sequence encoding the RNA-viral amplicon can be established by the action of said protein.

10. A system of controlling expression of a protein, comprising a genetically-modified multi-cellular plant organism and a signal for causing an expression of said protein, whereby said multi-cellular plant organism and said signal are designed such that expression of said protein can be initiated by externally applying said signal to said multi-cellular plant organism or a part thereof; said signal being a polypeptide having the activity of a site-specific recombinase, wherein the enzymatic activity of said protein is the same as the enzymatic activity of said polypeptide, and wherein said genetically-modified multi-cellular plant organism contains a heterologous nucleic acid and an additional heterologous nucleic acid in cells thereof, whereby said heterologous nucleic acid is adapted such that (a) expression of a protein from said heterologous nucleic acid can be caused in cells containing said heterologous nucleic and (b) said protein contains a protein portion enabling said protein of leaving a cell and entering other cells of said multi-cellular plant organism, wherein said protein portion is a domain of a viral movement protein, or a domain of a viral coat protein, and (c) said protein has a segment having a modifying activity, said segment having the activity of a site-specific recombinase rendering said heterologous nucleic acid expressible, whereby said protein causes expression of said protein from said heterologous nucleic acid in cells containing said heterologous nucleic acid, and (d) said protein controls transcription of an RNA-viral amplicon from said additional heterologous nucleic acid contained in cells of said multi-cellular plant organism; wherein, (i) the sequence encoding the RNA-viral amplicon is, in said additional heterologous nucleic acid, separated from a promoter by a sequence block that precludes an operable linkage between the sequence encoding the RNA-viral amplicon and the promoter; said sequence block being flanked by recombination sites such that said block can be cut out by a recombinase recognizing said recombination sites; or (ii) in said additional heterologous nucleic acid, a portion of a sequence necessary for transcription of the RNA-viral amplicon is in flipped orientation and flanked by recombination sites such that said sequence portion can flip back in correct orientation by a recombinase recognizing said recombination sites;

thereby, operable linkage for transcription of the sequence encoding the RNA-viral amplicon can be established by the action of said protein.

11. A stably or transiently genetically-modified multi-cellular plant organism or parts thereof obtained or obtainable by a method comprising the following steps:

(a) providing a multi-cellular plant organism or a part thereof, whereby cells of said multi-cellular plant organism or said part contain a heterologous nucleic acid encoding a protein, wherein cells of said multi-cellular plant or part thereof contain an additional heterologous nucleic acid; and (b) causing expression of the protein from said heterologous nucleic acid in at least some of said cells by delivering a polypeptide to the multi-cellular plant organism or part thereof, said polypeptide rendering said heterologous nucleic acid expressible, said polypeptide having the activity of a site-specific recombinase rendering said heterologous nucleic acid expressible;

wherein said protein (i) contains a protein portion enabling leaving a cell and entering other cells of said multi-cellular plant organism or a part thereof, wherein said protein portion is a domain of a viral movement protein, or a domain of a viral coat protein;

(ii) causes expression of said protein from said heterologous nucleic acid in cells containing said heterologous nucleic acid by a DNA modifying activity of a segment of said protein, said segment having the activity of a site-specific recombinase, wherein the enzymatic activity of said protein is the same as the enzymatic activity of said polypeptide; and (iii) controls transcription of an RNA-viral amplicon from said additional heterologous nucleic acid contained in cells of said multi-cellular plant organism or a part thereof;

wherein, a. the sequence encoding the RNA-viral amplicon is, in said additional heterologous nucleic acid, separated from a promoter by a sequence block that precludes an operable linkage between the sequence encoding the RNA-viral amplicon and the promoter; said sequence block being flanked by recombination sites such that said block can be cut out by a recombinase recognizing said recombination sites; or b. in said additional heterologous nucleic acid, a portion of a sequence necessary for transcription of the RNA-viral amplicon is in flipped orientation and flanked by recombination sites such that said sequence portion can flip back in correct orientation by a recombinase recognizing said recombination sites;

thereby, operable linkage for transcription of the sequence encoding the RNA-viral amplicon can be established by the action of said protein.

* * * * *